Figure 1A:
Figure 1D:
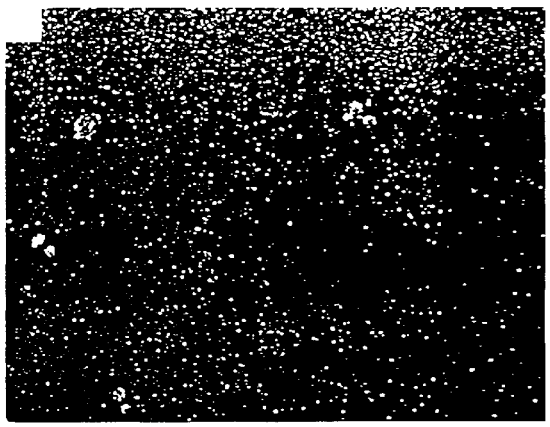
Figure 1B:
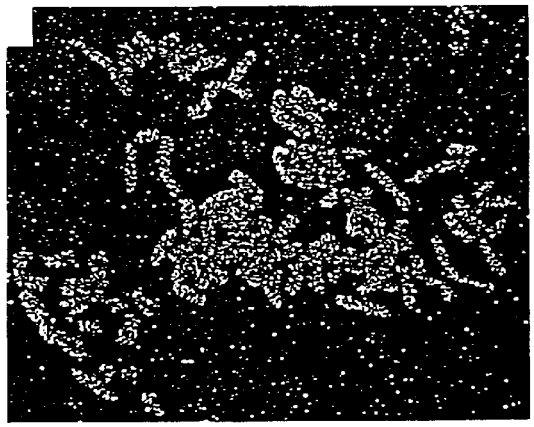
Figure 1E:
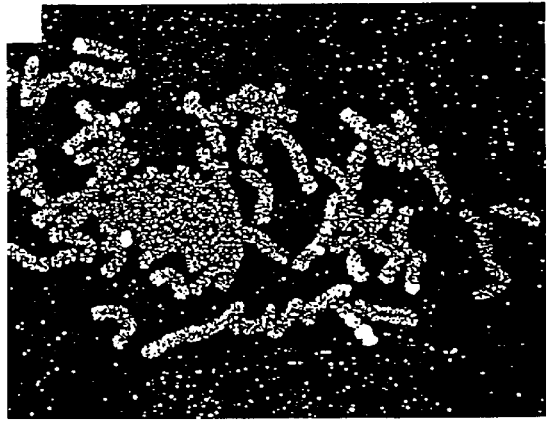
Figure 1C:
Figure 1F:
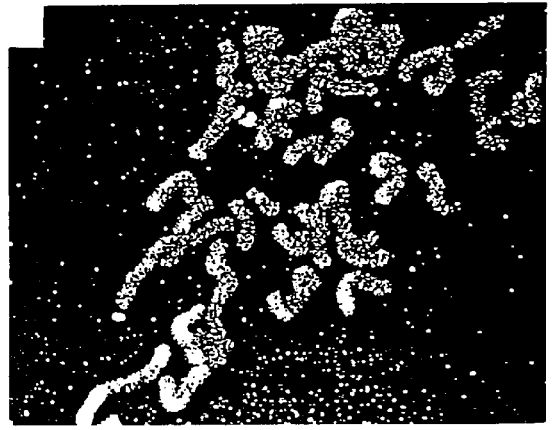
Figures 2I, 2J, 2K:
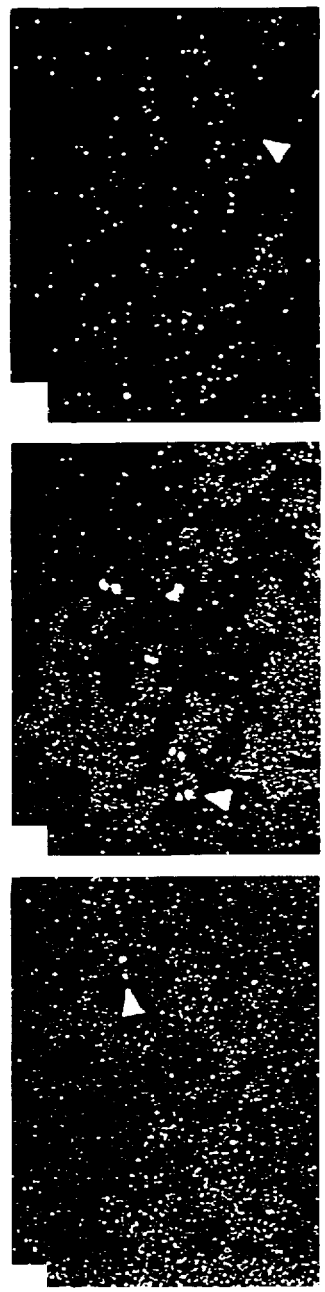

United States Patent [19]

Samulski et al.

[11] Patent Number: 5,773,289
[45] Date of Patent: Jun. 30, 1998

[54] AAV DIRECTED TARGETED INTEGRATION

[75] Inventors: Richard Jude Samulski; Xiao Xiao, both of Chapel Hill, N.C.

[73] Assignee: University of Pittsburgh, Pittsburgh, Pa.

[21] Appl. No.: 469,552

[22] Filed: Jun. 6, 1995

[51] Int. Cl.$^6$ .............................. C12N 15/63; C12N 5/00; C12N 15/00
[52] U.S. Cl. ................................... 435/320.1; 435/172.3; 435/325; 435/69.1; 514/44; 800/2; 935/23; 935/24; 935/32; 935/6; 935/55; 935/57; 935/70
[58] Field of Search .............................. 435/172.3, 320.1; 536/24.1; 800/2; 935/23, 24, 32, 6, 55, 57, 70

[56] References Cited

U.S. PATENT DOCUMENTS

| | | | |
|---|---|---|---|
| 4,797,368 | 1/1989 | Carter et al ........................... | 435/320.1 |
| 5,139,941 | 8/1992 | Muzyczka et al. ................... | 435/172.3 |
| 5,580,703 | 12/1996 | Kotin, et al. ......................... | 435/320.1 |

OTHER PUBLICATIONS

Promuga Protocols & Applications Guide (1991), p.27.
Levin, Genes IV (1990) p.552.
Zhou et al (1993). Experimental Hematology 21, 928–933.
Wulz et al (1992). J. of Virology 66, 2990–3002.
Bradley, A et al (1992). Biotechnology 10, 534–539.
Taeuish (1988). Science 240, 1468–1474.
Sambrook et al (1989). Molecular Cloning: A Laboratory Manual, 2nd ed. p.9.2.
Muzyczka, 1992, "Use of Adeno–Associated Virus as a General Transduction Vector for Mammalian Cells", Curr. Topics in Microbiology and Immunology 158: 97–129.
Samulski et al., 1991, "Targeted Integration of Adeno Associated Virus (AAV) Into Human Chromosome 19", Embo 12: 3941–3950.
Kotin et al., 1990, "Site–Specific Integration by Adeno–Associated Virus", Proc. Natl. Acad. Sci. USA 87: 2211–2215.
Friedmann, 1989, "Progress Toward Human Gene Therapy", Science 244: 1275–1281.
Tratschin et al., 1984, "A Human Parvovirus, Adeno–Associated Virus, as a Eucaryotic Vector: Transient Expression and Encapsulation of the Procaryotic Gene for Chloramphenicol Aceytltransferase", Mol. and Cell. Biology, 4: 2072–2081.
Mahy, et al., 1982, *Virus Persistence* (Cambridge University Press) pp.249–265.
Cheung et al., 1980, "Integration of the Adeno–Associated Virus Genome into Cellular DNA in Latently Infected Human Detroit 6 Cells", Virology 33: 739–748.

*Primary Examiner*—Jasemine C. Chambers
*Assistant Examiner*—Jill D. Schmuck
*Attorney, Agent, or Firm*—Pennie & Edmonds LLP

[57] ABSTRACT

The present invention relates to novel recombinant AAV (Adeno-associated virus) vectors that may be used to direct integration of recombinant DNA sequences into specific regions of the human host genome. These vectors may be used in gene therapies designed to replace or supplement defective genetic information with normal genetic information. The invention also relates to the isolation and characterization of the specific cellular host sequences, herein referred to as host target sequences, that signal the integration of AAV recombinant DNA sequences into specific regions of the host genome. Transgenic animals containing the generated target sequences may be as used as model is systems for testing of AAV based gene therapies.

20 Claims, 20 Drawing Sheets

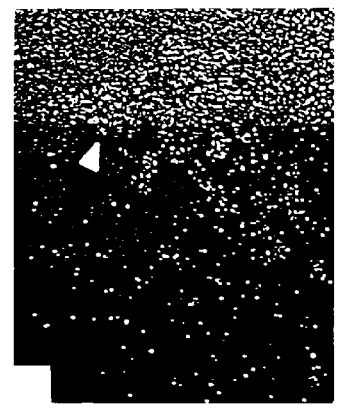 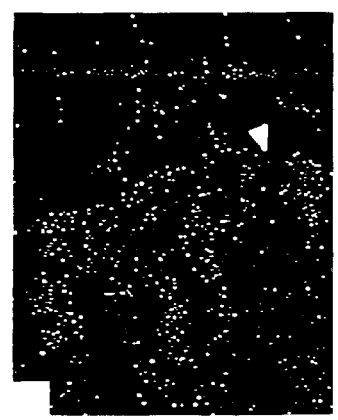 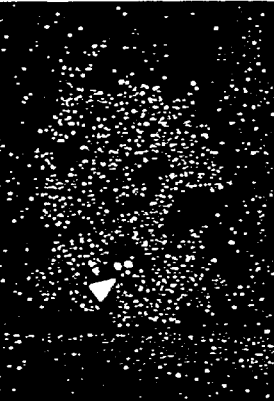 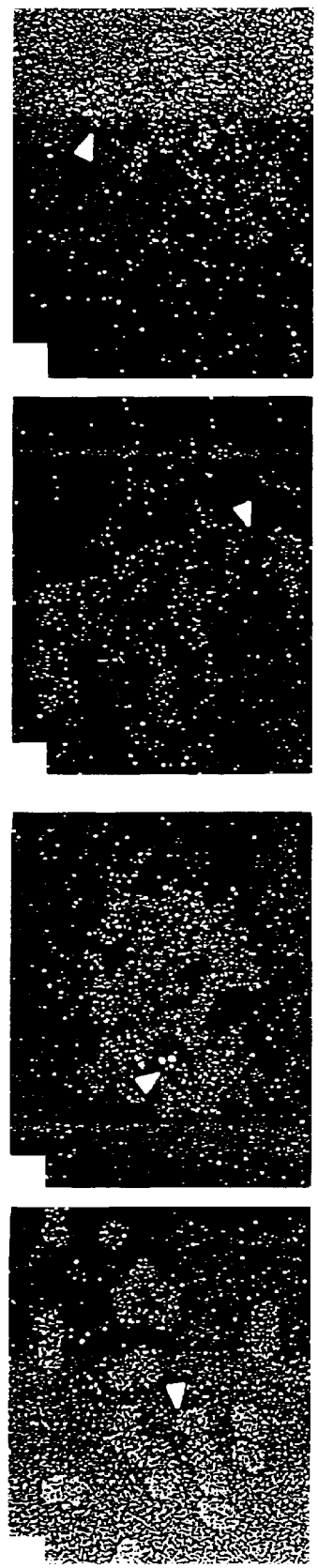 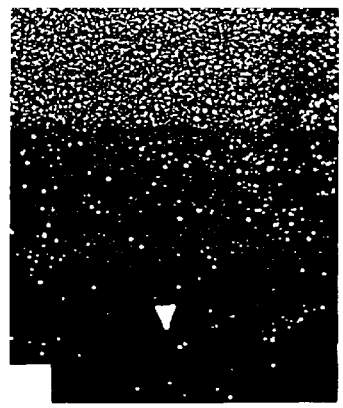 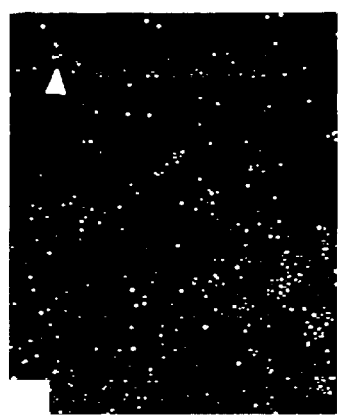 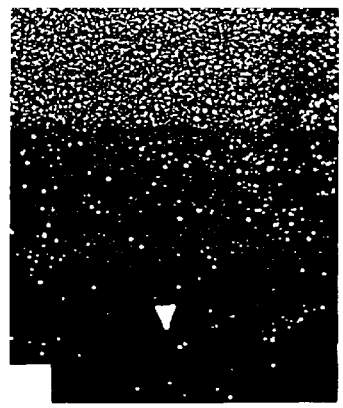 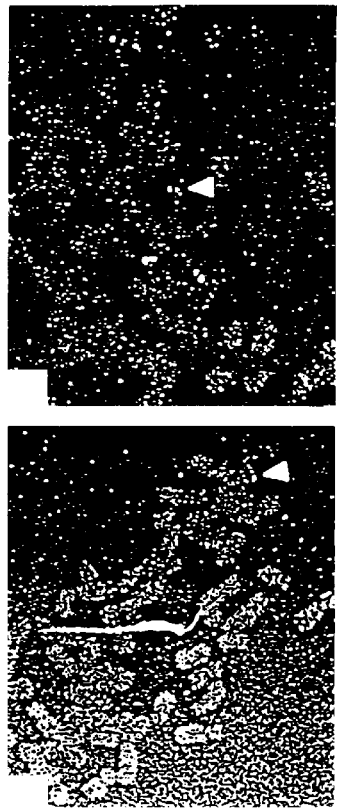
FIG.2A FIG.2B FIG.2C FIG.2D
FIG.2E FIG.2F FIG.2G FIG.2H FIG.3K  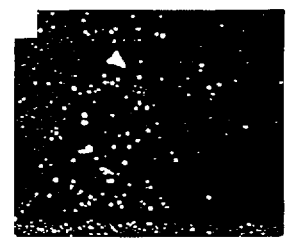 FIG.3L
FIG 3M 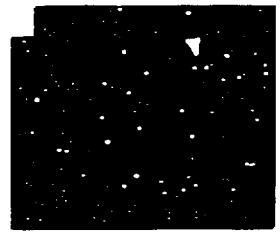 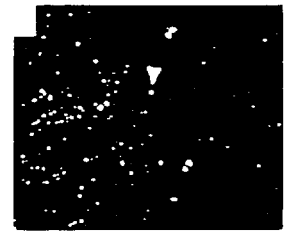 FIG 3N
FIG.3O  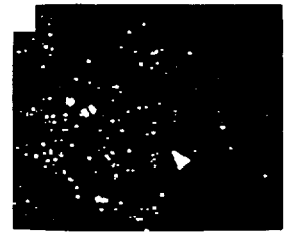 FIG.3P
FIG.3Q 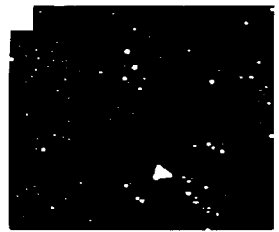 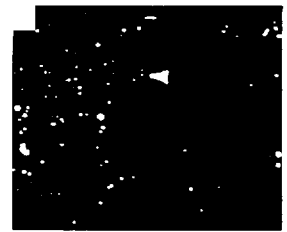 FIG.3R
FIG.3S 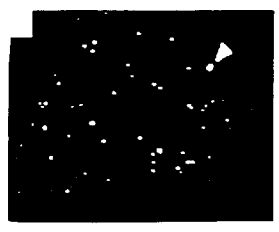 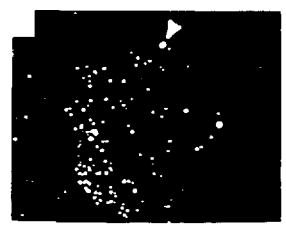 FIG.3T

LANE 1 2 3 4 5 6 7 ⎯⎯⎯⎯⎯⎯→ 29

```
                                    Mn l I
                                   Hae III
                                   Stu I
                                   Hae I
                                   Mse I
                    Mse I          Afl II                           Mse I
                      |             ||  || |                          |
AAACCCAACATCTTGACCTACCATTAAGCCCTTTCCCTTAAGGCCTCCAATAATTGAAACAAGTTTGCCCCTTAAATTAC   80
TTTGGGTTGTAGAACTGGATGGTAATTCGGGAAAGGGAATTCCGGAGGTTATTAACTTTGTTCAAACGGGGAATTTAATG
         .        .   |    .      ||  •|| |     .       .       .   • |     .
                     24          37                                  72
                                 38
                                 41
                                 41
                                 42
                                   44
```

```
                               Mse I
                    Pac I      Ase 1
           Rsa I    Mse I   Pac I
           Tth111 II  Mse I   Mse I                                 Ple I
Mnl I      Csp6 I   Ase I  Ase I                                    Hinf I
 |   |       |        |  ||    ||  ||                                 |
CCTCTTGCTTGTACCTTTAATTAATAATTAATTAATTCAATTCATTTGTCCACCCCAAAATTTACTTGAGTCCCACCTAT  160
GGAGAACGAACATGGAAATTAATTATTAATTAATTAAGTTAAGTAAACAGGTGGGGTTTTAAATGAACTCAGGGTGGATA
 |   |    •|    |   ||     || •||      .       .       .       |•          .
81       91       100   107                                    148
     86         97       108                                   148
           91          101   108
                    97          111
                                   112
```

FIG.13A

```
                    Alu I   Ssp I   Mbo I              Mbo II
                                                       Bbs I                       Bsr I          Alu I
GTCCCAAACCAATGTCCCAGCTTGAGAATATTTGGAAGAAGACCTGTCCCAGTTCTCCAAGTAGCTGAAATCCTTTGGGG  240
CAGGGTTTGGTTACAGGGTCGAACTCTTATAAACCTTCTTCTGGACAGGGTCAAGAGGTTCATCGACTTTAGGAAACCCC
                     |·|     |·|    |·|                                            |·|
                     179    187    195                                             209     223
                                    198
                                    198

Tfi I
                                                                       Hinf I
                                                                ScrF I
                                                                EcoR II
                                                                Dsa V
                                                                BstN I
                                            Mse I              Ple I  BsaJ I  BstK I    Tfi I
        Rsa I                                                  Hinf I                   Hinf I
        Csp6 I   Hph I              Xcm I
BspM I           Nla III
AAGCAGGTACATAGTATCGGCATGGTGATTAACCACAAGGGCTTTGGAGTCAGCCCTGATTCAGTCTTGATTCATATATT  320
TTCGTCCATGTATCATAGCCGTACCACTAATTGGTGTTCCCGAAACCTCAGTCGGGACCTAAGTCAGAACTAAGTATATAA
|·|              |·|              |·|             |·|             |·| |·|          |·|
243              260              272             286             294 293          309
247              263              268             286             294               309
                                                                  286                309
```

FIG.13B

```
              Ban II          Ava I      Mnl I    Taq I
         Nla IV  Taq I    Ban I   BamH I  Alw I Rma I    Mnl I
Rma I      EcoR I        Asp718                          Hinf I
  |          |    |  |      |       |    |    |   |       |
ATCACTAGGGGTTCCTGAATTCGAGCTCGGTACCCGGGGATCCTCTAGAGTCGACCAGTGTGGTTTGCAAGAGGAAGCA  560
TAGTGATCCCCAAGGACTTAAGCTCGAGCCATGGGCCCCTAGGAGATCTCAGCTGGTCACACCAAAACGTTCTCCTTCGT
  |          |    |  |      |       |    |    |   |       |               •
 485        497  503 509    513    518  522  525  528                     552
            •                                  •    •
 490        501  503 509    513    518  524                                
                                   518  525  528
                 503 509    514         
                 503        513         
```

FIG.13D

```
                           Rma I                                 HinP I                      Hae III
              Nla IV       BsiY I              Msc I             Hha I              MnI I   Bcn I
    EcoR I                                     Hae I    MnI I    BssH II            Dde I   Ava I
    |         | |          | |                 Eae I    |        |                  |       | |
GGGCGAATTCAGGAACCCTAGTGATGAGTTGGCCACTCCCTCACTGCGGCCTCGCTCGCTGCTCGAGGCGCCCGGGC  80
CCCGCTTAAGTCCTTGGGATCACTACTCAACGGTGAGGGAGTGACGCGGAGGCGAGGCGAGTGACTCCGGCGGGCCCG
    .         | |          .                   |   |    .       |                   |       | |
    5        12 19                             32  41           48                  65      74
                18                             32               48                  67      74
                                               32               48                  69
                                               33               49                  70
                                                                50                  70
                                                                50                  70
                                                                                    74

Sau3A I
                                                        Mbo I
                                                        Dpn II
                                                Stu I   Dpn I
    Dde I                                       Hae I                                        MnI I
    Alu I                                       |       |                  Acc I    BspW I   |
    Fok I                    Mae II     Mme I   Hae III |                  |        |        |
    | |                     |           |       |       |                  |        |        |
AAAGCTAAGGACTGGATGTAAGGCACAAGTCAAGTAGAACTGGAAGGCCTGATCTGTCTACACTGCAACCT  160
TTTCGATTCCTGACCTACATTCCGTGTTCAGTTCATCTTGACCTTCCGGACTAGACAGATGTGACGTTGGA
  . |                       .           .       |      .                  .         .        .
 83 85                      119         128    134    140                145       154      158
    91                                          134    140
    94                                          135    140
```

FIG.14A

FIG.14C

```
                                                          Sau3A I
                                                          Mbo  I
                                                          Dpn II
                                                          Dpn  I                              Hpa I
                                                          Alw  I             Mse I            Mse I
              Sau96 I       Mse I                         Sty I              Dra I            Hinc II
              Ava II        Ase I                         BsaJ I              ||    ||   ||    ||   560
TTGGATTTTTGAAATATGGTCCAAATTATTATTATTATACTTTTTCAACCAAGGGATCAATCTCTTTTAAAGGTT
AACCTAAAAACTTTATACCAGGTTTAATAATAATAATATGAAAAAGTTGGTTCCCTAGTTAGAGAAAATTCCAA
   •          ||       •   ||              •             |                 •||   551  558
              498          512                            534                   552        559
              498          513                            534               539            558
                                                                            540
                                                                            540
                                                                            540
                                                                            540
```

FIG.14D

AAV DIRECTED TARGETED INTEGRATION

1. INTRODUCTION

The present invention relates to novel recombinant AAV (Adeno-associated virus) vectors that may be used to direct integration of recombinant DNA sequences into specific regions of the human host genome. These vectors may be used in gene therapies designed to replace or supplement defective genetic information with normal genetic information. The invention also relates to the isolation and characterization of the specific cellular host sequences, herein referred to as host target sequences, that signal the integration of AAV recombinant DNA sequences into specific regions of the host genome. Transgenic animals containing the generated target sequences may be as used as model systems for testing of AAV based gene therapies.

2. BACKGROUND OF THE INVENTION

2.1. Gene Therapy

At the present time, treatments for most genetic diseases do little to alleviate the symptoms associated with the genetic disease and considerable effort is currently underway to develop new, safe and effective methods of treatment. Recent progress in the areas of molecular biology and genetic engineering have lead to the isolation and characterization of genes associated with genetic diseases. This in turn has lead to the development of the concept of gene therapy, i.e., the replacement or supplement of defective genetic information with normal functional genes, and its potential use for treatment of genetic disorders.

The most well developed model systems for transfer of new genetic information and correction of diseased phenotypes have involved the use of recombinant pathogenic viruses such as the RNA and DNA tumor viruses. While many of these viruses are pathogenic and capable of causing disease it has been proposed that these viruses could be genetically manipulated to deprive them of their deleterious characteristics while maintaining their usefulness for introduction of stable, inheritable and functionable genetic information into infected mammalian cells.

The retroviruses have been extensively studied as a class of viruses for use in gene therapy (Miller, A. D., 1990, Human Gene Ther. 1:5–14). Unfortunately, there are a number of disadvantages associated with the use of retroviruses which include the random integration of viral DNA into the host chromosome which can lead to insertional mutagenesis. In addition, the long terminal repeat (LTR) structures located at the ends of the retroviral genome contain promoter/enhancer activity that may lead to activation of genetic loci located adjacent to the integrated viral DNA. For example, integration of retroviral DNA adjacent to a proto-oncogene may lead to inadvertent activation of proto-oncogene expression which may, in turn, lead to transformation and tumorigenesis.

In addition to the retroviruses, the adenovirus associated viruses have also been studied as an alternative system for delivery of stable genetic information into the cell. The construction of recombinant vectors containing AAV DNA and heterologous genes under the control of the AAV transcription promoter are described in Carter et al. U.S. Pat. No. 4,797,368. Muzyczka et al., U.S. Pat. No. 5,139,942 describe, recombinant vectors in which heterologous DNA under the control of promoters other than the AAV promoter are ligated into vectors containing at lease the first and last 145 base pair terminal repeats.

The development of viral vectors for use in the efficient transfer of functional genes stably into human cells continues to be a major goal for investigators studying genetic correction of human disease.

2.2. Adeno-Associated Virus

Adeno-associated virus (AAV) is a defective parvovirus composed of a linear single-stranded DNA molecule of 4680 nucleotides which contains major open reading frames coding for the REP (replication) and CAP (capsid) proteins. The REP proteins function during replication of the viral genome, while the CAP proteins assemble to form the viral capsid molecules into which the viral genome is packaged. Flanking the AAV coding regions are two 145 nucleotide inverted terminal repeat sequences (ITRs) that contain palindromic sequences that can fold over to form hairpin structures that function as primers during initiation of DNA replication. In addition to their role in DNA replication, the ITR sequences have been shown to be necessary for viral integration, rescue from the host genome and encapsidation of viral nucleic acid into mature virions. (Muzyczka, N., 1992, Current Topics in Microbiology & Immunology 158:97–129.)

In the presence of helper virus, AAV will enter the lytic pathway whereby the viral genome is transcribed, replicated and encapsidated into newly formed viral particles. In the absence of helper virus function, the AAV genome becomes integrated as a provirus into the host cell genome through recombination between the AAV termini and host cell sequences. (Cheung, A. et al., 1980, J. Virol. 33:739–748; Berns, K. I. et al., 1982, in Virus Persistence, eds. Mahey, B. W. J., et al. (Cambridge Univ. Press, Cambridge), pp. 249–265). Characterization of the proviral integration site and analysis of the flanking cellular sequences indicates specific targeting of wild type AAV viral DNA into the long arm of chromosome 19. (Kotin, R. M. et al., 1990, Proc. Natl. Acad, Sci. U.S.A. 87:2211–2215; Samulski, R. J. et al., 1991, EMBO J. 10:3941–3950).

Recently, it has been demonstrated that when an intact AAV genome is cloned into a prokaryotic vector and is transfected into cells, in the presence of helper virus, AAV will be rescued out from the plasmid vector and enter the lytic pathway leading to production of mature virions. In the absence of helper virus the recombinant AAV vector will integrate into the host cell genome and remain as a provirus until the cell subsequently becomes infected with a helper virus.

3. SUMMARY OF THE INVENTION

The present invention is directed to genetically engineered vectors designed to introduce and/or express a heterologous gene of interest in a desired host. The recombinant vectors of the invention may be used to target integration of recombinant DNA into specific regions of the human host genome.

The invention is based, in part, on the discovery that, in contrast to wild type AAV vectors which target integration into chromosome 19, novel vectors described herein target integration into other unique sites of the genome which include chromosomes 2, 12, 22 and a D-group chromosome. The expression of integrated heterologous DNA sequences can be influenced by their chromosomal environment, therefore, vectors which target to unique sites in the host genome may be selected depending on the desired level of expression. For example, some sites in the genome will actually favor low level expression of an integrated gene, while other sites may allow unregulated expression of that gene. In addition, the level of expression at any one particular site, may be dependent on the cell type or tissue in which integration takes place. Construction of targeting vectors that integrate efficiently into specific chromosomal locations represents a significant improvement over other viral vector systems developed for use in gene therapy such as retroviruses, where integration into the host genome is completely random.

In the vectors of the invention, the gene of interest is flanked at both ends with AAV sequences. The targeting vectors contain all the necessary information, in cis, for converting a circular duplex DNA molecule into a linear replicating molecule with covalently closed ends, and for encapsidation into AAV virions or integration into specific regions on the host genome.

A system for replication and packaging of the novel recombinant vectors into mature AAV virions is described. The resulting recombinant viral stocks provide a convenient and efficient means for transfer of genetic information into any cell or tissue of choice. The vectors of the invention may be used in gene therapies where the desired goal is the correction of genetic defects by transfer and expression of a normal or wild type complement of a defective gene into a specific region of the human genome.

The invention also relates to the specific cellular host sequences that act as host target sites for integration of the novel AAV vectors. For example, the specific regions of chromosomes 2, 12, 22 and the D chromosome where the novel AAV vectors integrate, represent host target sites. These sites may be identified by isolation and characterization of the DNA sequences found adjacent to integrated AAV vector DNA. Once identified, the human target sequences may be used to engineer transgenic animals containing the human target sites incorporated into their own genome. Such transgenic animals may be used for development and testing of new AAV based genetic therapies.

4. BRIEF DESCRIPTION OF THE FIGURES

FIGS. 1A–F. In situ chromosome analysis of wild-type AAV latent cell lines. Detection of AAV provirus at the tip of one chromosome in the latent cell line H3 (panel A, red signal), G11 and D5 (panels B and C, yellow signal) using AAV-specific probe. Colocalization of AAV provirus to chromosome 19 by in situ analysis using both AAV and chromosome 19 specific probe (panels D, E, and F, double dots). Panel A and D chromosomes were counterstained with DAPI (blue), whereas panels B, E, C, and F were counterstained with propidium iodide (red). All DNA probes were indirectly labeled with FITC, except the AAV probes used in panel A and D which were labeled with Cy3 (a rhodamine-like dye with red color).

FIGS. 2A–K. In situ chromosome analysis of mutant REP$^-$ CAP$^-$ neo AAV latent cell lines. The chromosomes were hybridized with a neo probe in all panels. Other chromosome specific probes were also utilized to detect the specific chromosomes. The arrow head highlight the neoAAV proviruses. Cell line S102 was shown in Panel A and B on chromosome 19; Cell line S110 in panels C and D on chromosome 12; Cell line S101 on chromosome 22; Cell line S111 in panel G and H on chromosome 2; Cell line neo2Sc #2 and #3 were shown in panel I, J and K on a D-group chromosome.

Figure 3A:
Figure 3B:
Figure 3C:
Figure 3D:
Figure 3E:
Figure 3F:
Figure 3G:
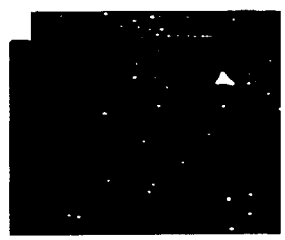
Figure 3H:
Figure 3I:
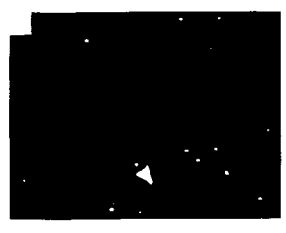
Figure 3J:
Figure 4A:
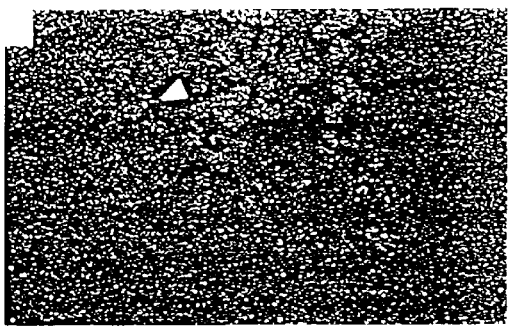
Figure 4B:
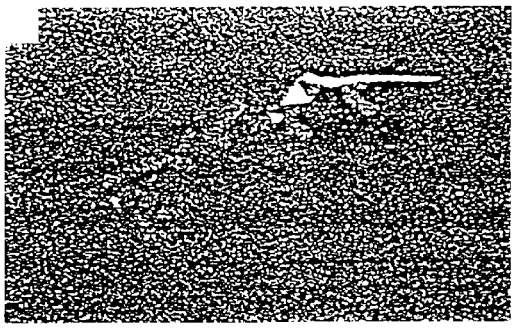
Figure 4C:
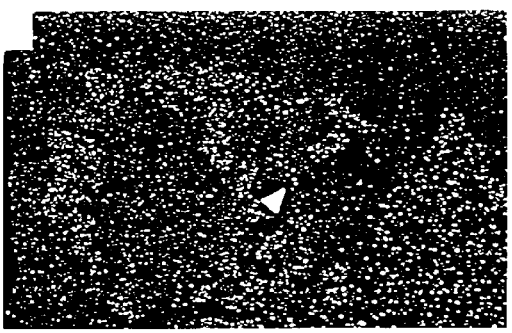
Figure 4D:
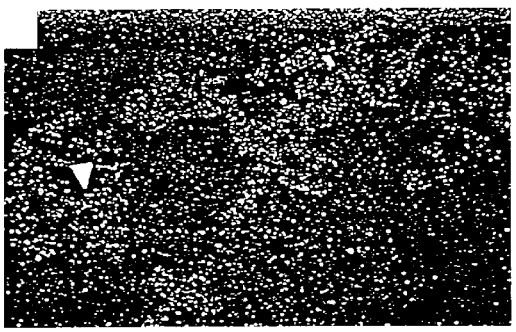
Figure 4E:
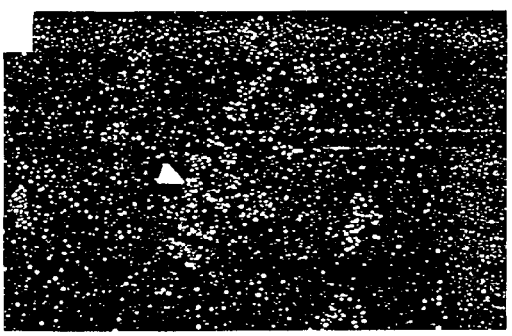
Figure 4F:
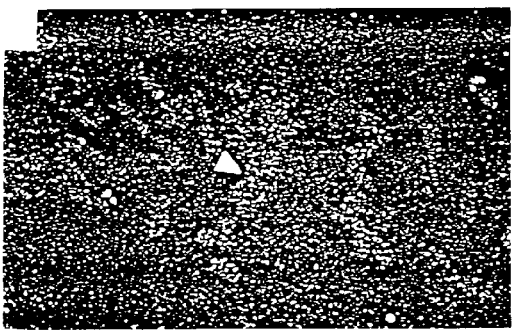
Figure 4G:
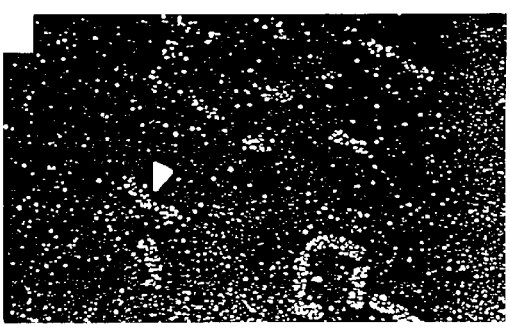
Figure 4H:
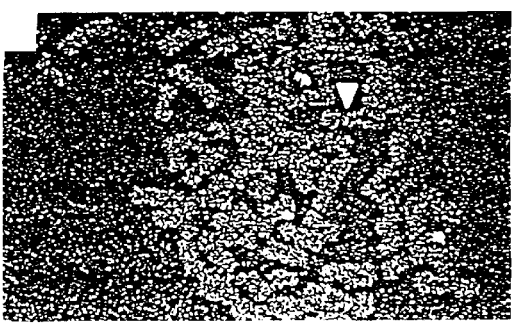

FIGS. 3A–T. In situ hybridization of the mutant REP$^+$ CAP$^-$ neo AAV integration. In panel A, C, E, G, I, K, M, O, Q and S, neo probe was used to detect the neo-AAV. In Panel B, D, F, H. J. L. N. P, R and T, both neo and chromosome 19 probe were used to identified chromosome 19. In two cell lines HN63 (A & B) and XHN-4 (C & D), AAV provirus was detected on chromosome 19. For the other cell lines, AAV proviruses were not detected on chromosome 19.

FIGS. 4A–H. In situ hybridization of the mutant REP$^-$ CAP$^+$neo AAV integration. In panel A, C, E and G neo probe was used to detect the neo-AAV. In Panel B, D, F and H both neo and chromosome 19 probe were used to identified chromosome 19. In one cell line XCB-2 (A & B), AAV provirus was detected on chromosome 19. For the other cell lines, XCB-5, (panel C & D); XCB-7, (E & F); XCH-2, (G & H); AAV provirus was not detected on chromosome 19.

Figures 5A, 5B:
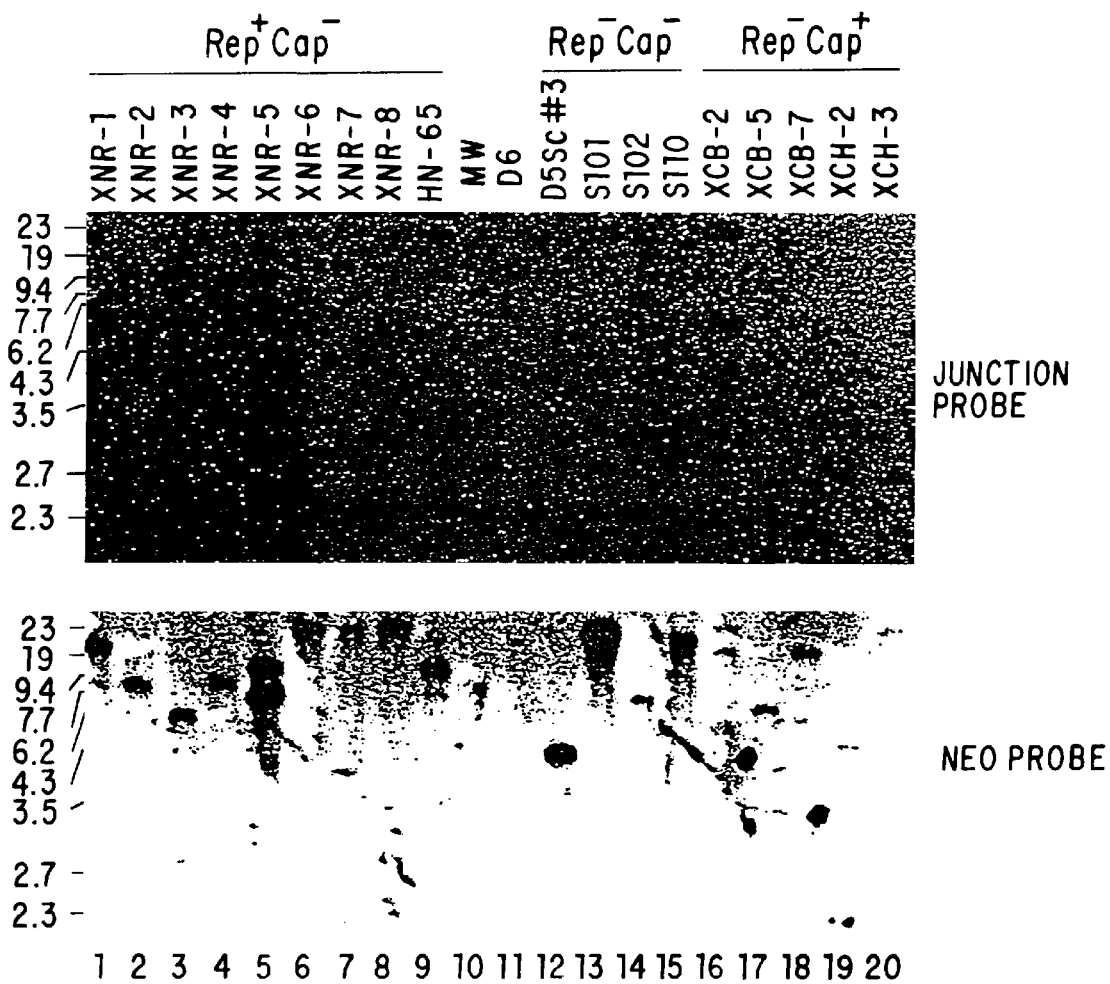

FIG. 5 Analysis of mutant neo-AAV integrations in multiple independent latent cell lines. Each lane contains 5 ug of genomic DNA isolated from various independently derived AAV latent cell lines digested with Bam HI and fractionated on a 1% agarose gel. Filters were first probed with the cellular sequences (Samulski, et al., 1992) (panel indicated "junction probe"), and then stripped and reprobed with neo-specific sequences (panel indicated "neo-probe"). Molecular weight markers (in kilobases) are indicated.

Figure 6:
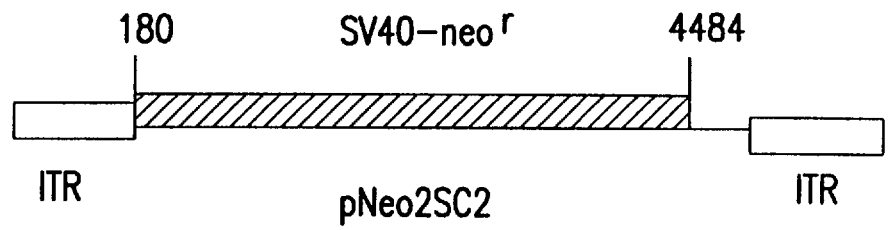

FIG. 6. Adeno-associated viral DNA sequences and SV40-neo$^r$ sequences contained in the recombinant vector designated pNeo2SC2.

Figure 7:
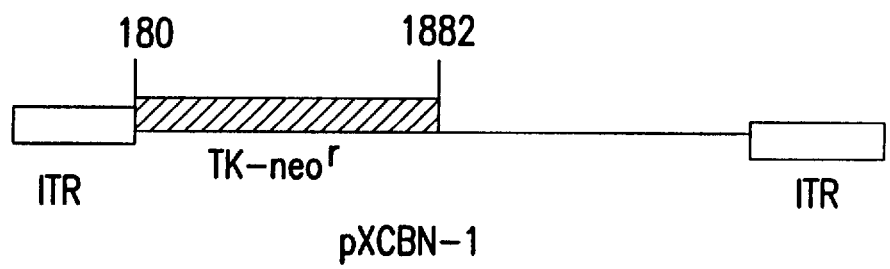

FIG. 7. Adeno-associated viral DNA sequences and TK-neo$^r$ sequences contained in the recombinant vector designated pXCBN-1.

Figure 8:
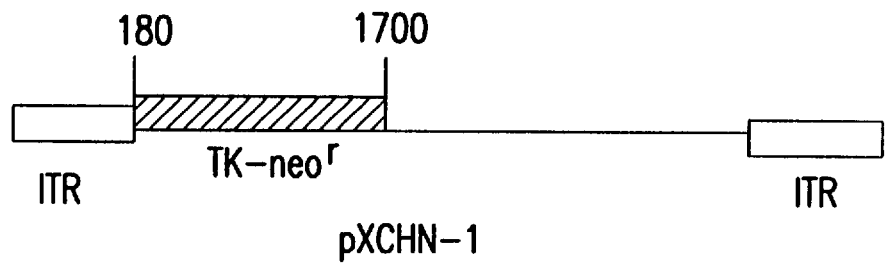

FIG. 8. Adeno-associated viral DNA sequences and TK-neo$^r$ sequences contained in the recombinant vector pXCHN-1.

Figure 9:
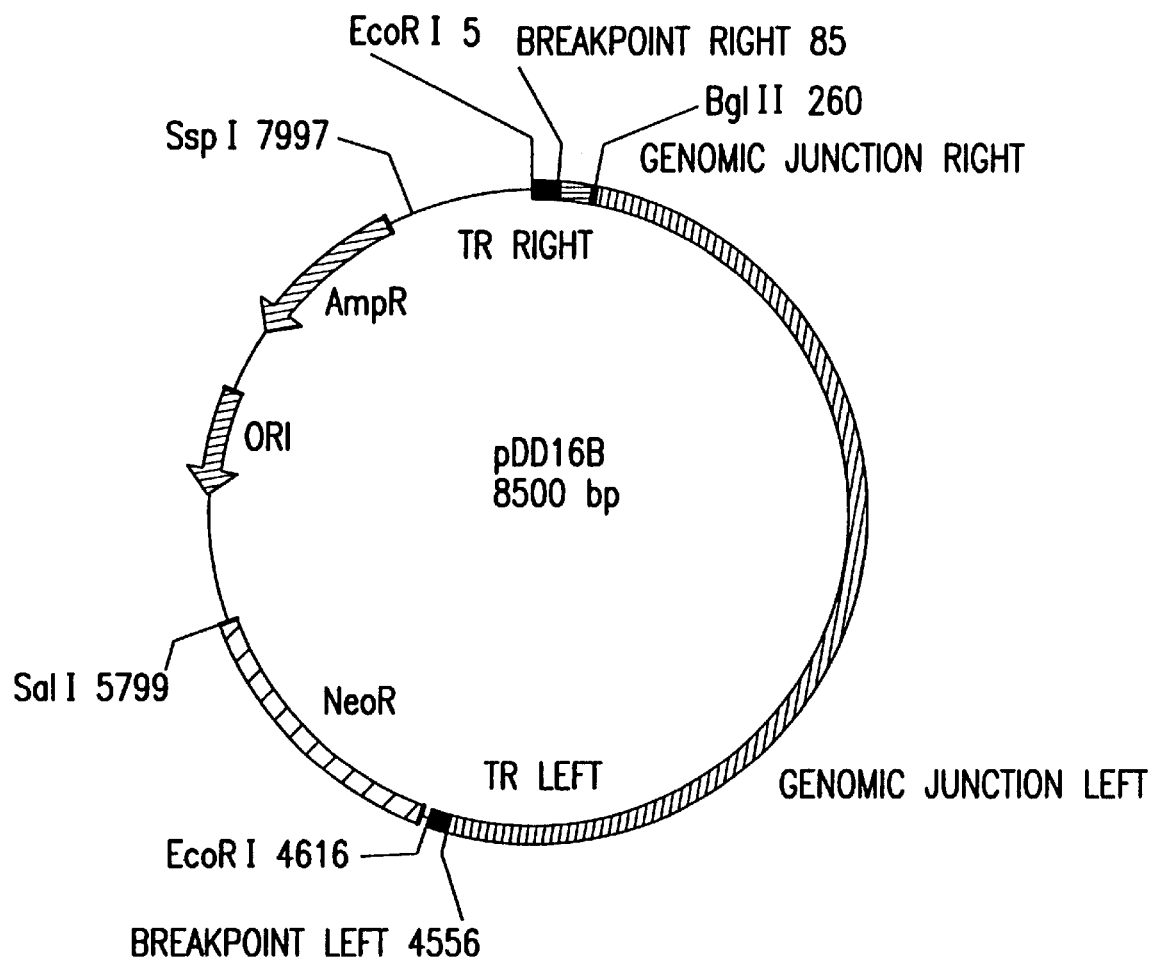

FIG. 9. Plasmid map of pDD16B.

Figure 10:
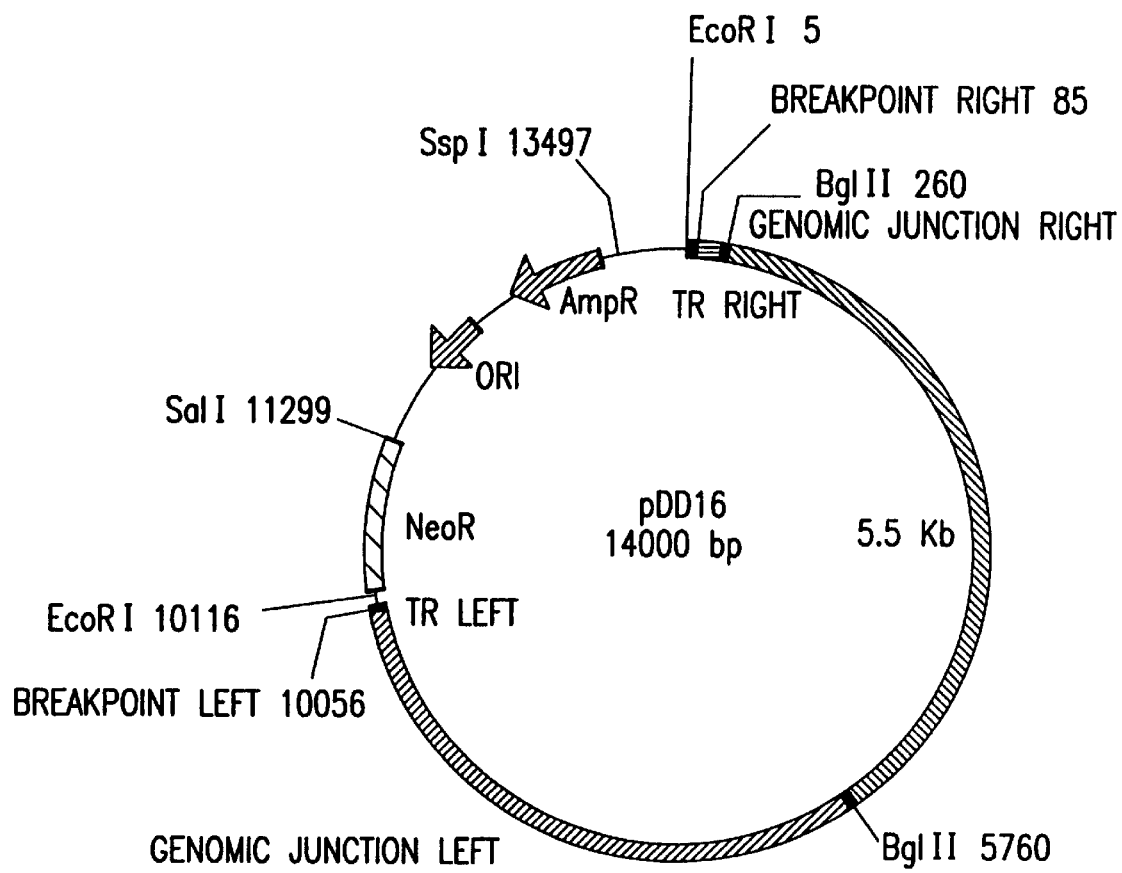

FIG. 10. Plasmid map of pDD16.

Figure 11:
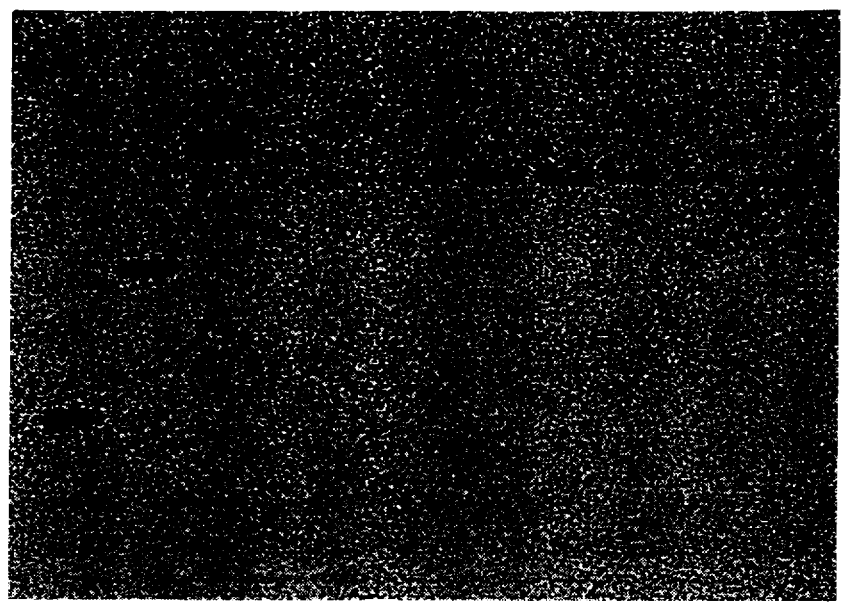

FIG. 11. Southern Blot analysis of DNA from latent cell lines containing the pDD-Neo provirus. The probe used is a 500 basepair DNA fragment from the left-hand junction of pDD-Neo and the chromosome derived from the 9.5 kb proviral clone pDD16B. Lane 1: 1.6 kb pBR322 DNA fragment. Lane 2: 3.9 kb EcoRI fragment od pDD-Neo. Lane 3: DNA from pDD116B, the 9.5 kb proviral clone from DD-16 containing pDD-Neo and 5.5 kb of genomic DNA. Lane 4: Empty. Lanes 5–11: Bgl II digests of genomic DNA from latent cell lines containing the pDd-Neo provirus. Lane 5: Cell line DD1. Lane 6: Cell line DD2. Lane 7: Cell line DD5. lane 8: Cell line Dd13. Lane 9: Cell line DD14. Lane 10: Cell line DD16. lane 11: Cell line DD18. Lane 10 contains genomic DNA from which the cline pDD16B was originally derived.

Figure 12:
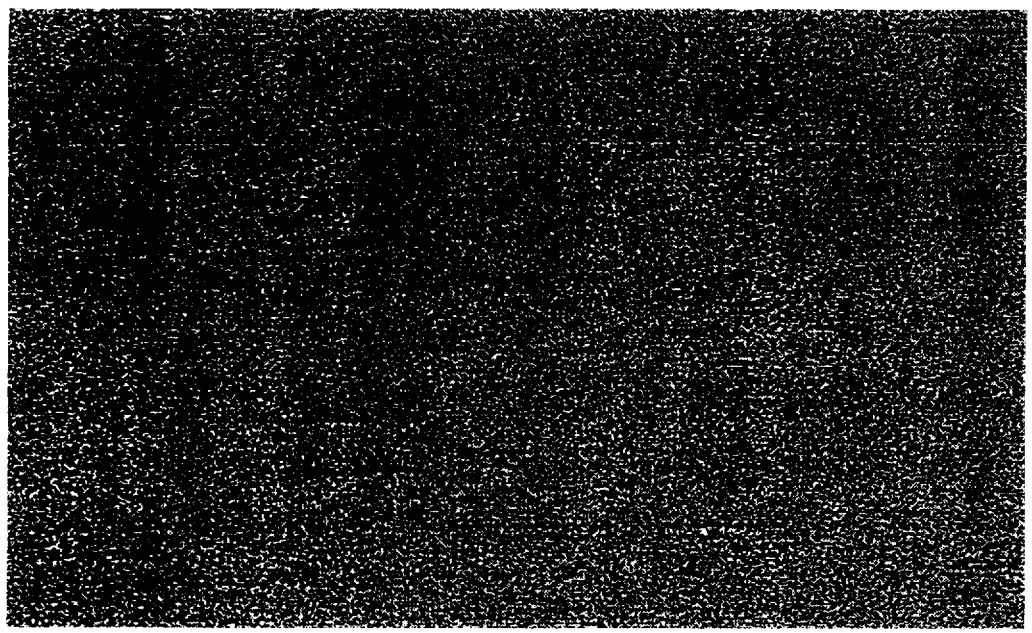

FIG. 12. Southern Blot analysis of somatic cell hybrid panels containing DNA from individual human chromosomes (Oncor, Inc. Gaithersburg, Md.) containing Bam HI digested DNA. The probe used is the same 500 basepair probe as described in FIG. 1. Lane 1: Total genomic DNA, human male. Lane 2: Total genomic DNA, human female. Lane 4: Total genomic DNA, Mouse. Lane 5: Total genomic DNA, Hamster. Lane 6: Human chromosome 1 DNA. Lane 7: Human chromosome 2 DNA. Lanes 8–29 (no hybridization) contain DNA from chromosomes 3–22, X and Y.

Figure 13C:
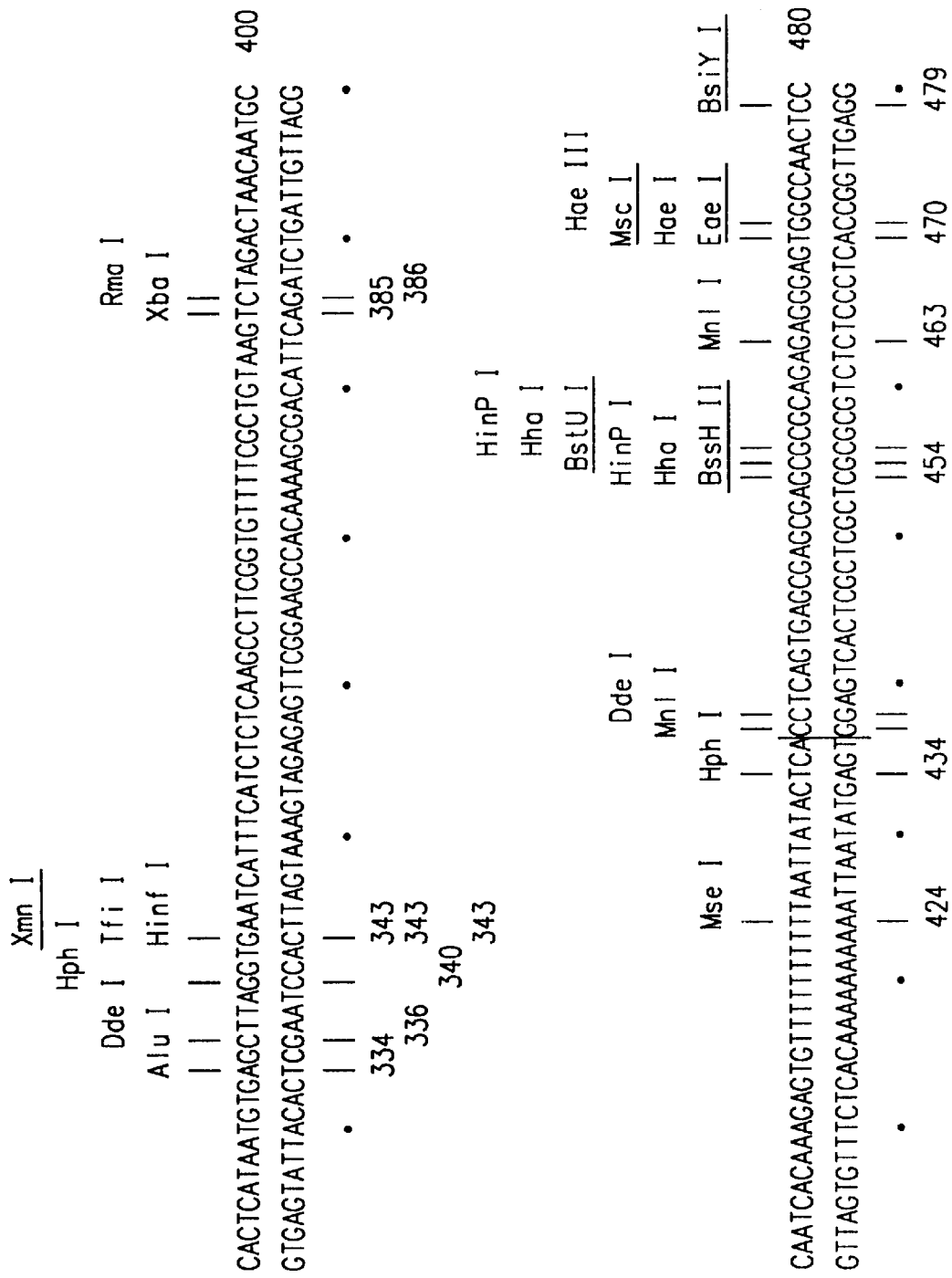

FIGS. 13A and 13B. Sequence and Restriction Map of pDD16B Left Junction.

Figure 14B:
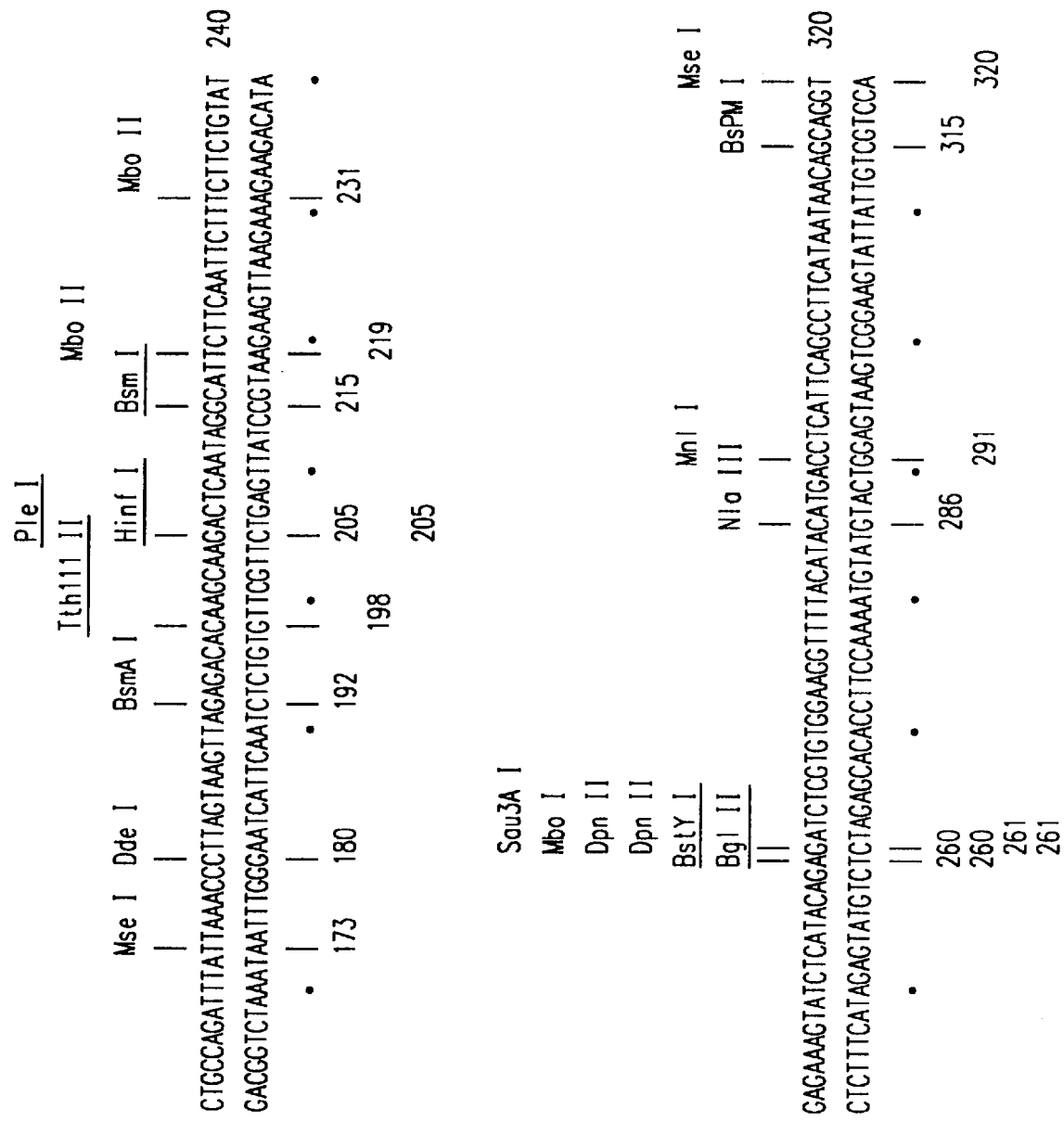

FIGS. 14A and 14B. Sequence and Restriction Map of pDD16B Right Junction.

5. DETAILED DESCRIPTION OF THE INVENTION

The present invention is directed to genetically engineered vectors designed to introduce and express a heterologous gene of interest in mammalian cells. More specifically, the invention is directed to recombinant vectors that contain novel AAV viral sequences which direct the integration of recombinant vector DNA into unique specific regions of the human chromosome. The invention is based, in part, on the discovery that, in contrast to recombinant vectors containing wild type AAV sequences which integrate into human chromosome 19, recombinant AAV vectors lacking viral coding regions, integrate with an increased frequency into additional chromosomal regions of the human genome. In particular, the engineered vectors of the invention direct integration of recombinant vector DNA into unique regions of the human genome, including sites located on chromosomes 2, 12, 22 and a D-group chromosome.

The invention is described by way of examples in which recombinant expression vectors were constructed which contained deletions of the AAV viral REP and CAP coding sequences. Using techniques such as in situ hybridization and Southern Blot analysis, the referred sites of integration were analyzed and found to be sites on chromosomes other than chromosome 19.

The AAV vectors of the invention may be used as viable alternatives to other viral systems, such as retroviral systems, which have been developed for use in gene therapy. The recombinant vectors described herein may be designed and genetically engineered to transfer genetic information into specific regions of the human genome, and to express the wild type complement of any given defective gene.

In addition, the novel human AAV integration sites or human target sites, can be used to bioengineer transgenic animals containing the target sequences incorporated into their genome. The resulting transgenic animals may be used as animal model systems for testing of gene therapies that rely on the use of recombinant AAV vectors for correction of genetic defects.

5.1. Characterization of Recombinant AAV Integration

A substantial amount of evidence has been generated which demonstrates site-specific integration of wild type AAV into human chromosome 19. To confirm these results, three latent cell lines infected with wild type AAV were examined by fluorescent in situ hybridization. One cell line designated Detroit 5 (Berns et al., 1975) was established 17 years ago from a human lung carcinoma cell line. The other two cell lines, G11 and H3, were derived from AAV infected HeLa cells. As expected, in all three cell lines tested, the AAV viral DNA produced a signal on the tip of the q arm of chromosome 19 (FIG. 1).

Very little is known about the identities of cis-elements and trans factors responsible for specific integration of wild type AAV into chromosome 19. To investigate the possible role of the viral REP and CAP proteins in site specific integration, a number of viral vector mutants were constructed and analyzed. For the convenience of single cell cloning, a neo-resistant gene was built into the mutant vectors as a dominant marker for G418 selection. Recombinant viral stocks were used to determine preferred sites of integration into the host cell genome. The integration sites were initially characterized by performing in situ fluorescent hybridizations using, for example, either biotin or fluorescent tagged Neo$^r$ sequences, to distinguish the recombinants from wild-type AAV.

In a specific embodiment, described herein, recombinant AAV constructs were made by either deleting the entire REP and CAP genes or maintaining the REP or CAP proteins. The resulting vectors also contained the neo$^r$ gene inserted between the two viral ITR sequences along with an additional 140 basepairs of non-coding AAV sequence. Virus stocks were prepared with a helper plasmid that codes for the REP and CAP proteins. Cells were infected with the recombinant viruses and neomycin resistant clones were selected by addition of G418 into the tissue culture medium. Independent neo resistant cell lines were subjected to in situ florescent hybridization to determine on which chromosome the AAV vector had integrated.

A REP$^-$CAP$^-$ recombinant AAV construct was made by deleting the entire REP and CAP genes and substituting them with a neomycin resistant (neo$^r$) gene. The resulting recombinant contains one ITR on the left side, a neo$^r$ gene in the middle and one ITR plus 140 basepair non-coding AAV sequence on the right side. This virus stock was prepared with a helper pAAV/Ad, which does not contain ITRs but codes for the REP and CAP genes. Detroit 6 cells were infected with the virus and a selection was carried out for G418 resistant clones.

Five independent G418 resistant cell clones were subjected to in situ fluorescent hybridization with either biotin-labeled neo probe alone or neo probe plus chromosome 19 probe (Epstein et al., 1987). One out of the five cell lines tested had the neo-AAV integrated into chromosome 19, similar to wild type AAV (FIG. 2, panel A & B for cell line S102). The remainder of the cell lines had the neo-AAV integrated on different chromosomes as identified either by chromosome-specific probe or by chromosome banding and morphology. The results are shown respectively in FIG. 2, panel C & D for clone S110 on chromosome 12; panel E & F for clone S101 on chromosome 22; panel G & H for clone S111 on chromosome 2; and panel I & J for clones D5neo Sc#3 and panel K for D5neo Sc#2 on a D-group chromosome. Since clones from panel I, J and K are different sub-clones from one original cell line derived from Detroit 5 cells, they should be considered as one. For panel K, neo and AAV probes were simultaneously used and the wild type AAV could be easily observed on chromosome 19, while the neo-AAV had a much weaker signal, suggesting that the neo-AAV had a lower copy number. The above results suggest that the inverted terminal repeat contains cis-sequences which can mediate site-specific integration, although with a lower frequency of 20% (⅕) as revealed by in situ hybridization.

A Rep$^+$Cap$^-$ neo-AAV mutant vector was made by replacing the Cap gene with neo$^r$ gene while leaving Rep gene fully functional (Hermonat and Muzyczka, 1984). REP$^+$CAP$^-$neo-AAV cell clones were produced by G418 selection and subjected to in situ hybridization. Ten cell lines were assayed. Two of them had the neo virus integrated into chromosome 19 (FIG. 3, panel A & B for clone HN63 and C&D for clone XNR-4. In the remaining eight clones, the REP$^+$CAP$^-$ neo-AAV's were not integrated into chromosome 19 (FIG. 3, panel E through T). For instance, Clone XNR-2 (panel G & H) had the neo virus on a site near the centromere of a chromosome morphologically like chromosome 5. Clone XNR-3 (panel I & J) had the virus at the middle of the p arm of a chromosome like chromosome 2, similar to the case in clone S111 (REP$^-$CAP$^-$, FIG. 30, panel G & H). Clone HN21 (panel S & T) had the neo-virus on a double minute, in which case the common AAV integration target sequence has been disrupted by the virus as previously revealed through southern blot (Kotin et al., 1990). Based on the fact that common fragile sites on 19q13 have been reported (Yunis and Soareng, 1984; Yunis et al., 1987), this double minute could be derived from chromosome 19 under drug selection.

These results demonstrated that the functional Rep gene in a mutant neo-AAV virus did not increase the integration efficiency into chromosome 19. Similar to REP CAP$^-$ neo-AAV, the chromosome 19 specific integration efficiency by REP+CAP−neo-AAV is about 20% (²/₁₀), possibly 30% (³/₁₀) if the HN21 case is counted as a positive result. In contrast, the wild type AAV had a specificity greater than 80%. Two mutant constructs were made by replacing the Rep gene with neo gene while retaining the capsid gene intact. In one plasmid, referred to as pXCHN-1 the p40 promoter is deleted resulting in a promoterless capsid gene (FIG. 8). The other plasmid which retains a functional p40 promoter is referred to as pXCBN-1 (FIG. 7). The Rep⁻Cap⁺ neo-AAV viruses were prepared by conventional method. Human Detroit 6 cells were infected by the recombinant viruses and the G418 resistant single clones were isolated. The clones made from the virus with the functional p40 promoter are named XCB-1 through XCB-12, while the ones made from the promoterless capsid virus are named XCH-1 to 10.

Five G418 resistant clones were examined by in situ chromosome hybridization and were found to have a similar specific integration efficiency into chromosome 19 at about 25% (¼) revealed by fluorescent in situ hybridization (FIG. 4).

Although fluorescent in situ hybridization can directly visualize the physical location on the chromosomes at the microscopic level, it does not have the sensitivity and resolution at the molecular level when compared with Southern Blot analysis.

In order to confirm the in situ fluorescent hybridization results, those neo-AAV latent cell lines already analyzed by in situ hybridization were further characterized by genomic Southern Blot. The genomic DNAs from various neo-AAV cells were digested with restriction enzyme BamHI and probed with a cloned common AAV-cellular junction fragment located on chromosome 19, which displays as a single 2.6 kb BamHI band by southern blot in the parental cells but is disrupted in about 80% of the wild type AAV latent cell lines (Kotin et al., 1990, Samulski et al., 1991). After probing with the junction fragment, the same blot was stripped with sodium hydroxide and reprobed with the neo probe. The southern hybridization results of the mutant AAV cell lines are shown in FIG. 5 and confirm the in situ fluorescent hybridization results. A summary of the in situ hybridization and Southern Blot analysis is presented in Table 1.

TABLE 1

Summary of characterization of AAV integration

| Cell line | Rep+/− | Cap+/− | In situ[a] | Southern[b] | Rescue |
|---|---|---|---|---|---|
| D5 | + | + | 19/q13.4 | + | high |
| G11 | + | + | 19/q13.4 | + | high |
| H3 | + | + | 19/q13.4 | + | high |
| M19 | + | + | 19/q13.4 | + | high |
| M21 | + | + | 19/q13.4 | + | high |
| XNR-1 | + | − | ? | − | high |
| XNR-2 | + | − | 5/q12–q13 | − | high |
| XNR-3[c] | + | − | 2/p16–p21 | − | no |
| XNR-4 | + | − | 19/q13.4 | + | low |
| XNR-5 | + | − | ? | + | no |
| XNR-6 | + | − | ? | − | no |
| XNR-7 | + | − | D-group/q2–q3 | − | no |
| XNR-8 | + | − | ? | − | no |
| HN63 | + | − | 19/q13.4 | + | no |
| HN21 | + | − | DM | − | high |
| XCB-2 | − | + | 19/q13.4 | + | ND |
| XCB-5 | − | + | ? | − | ND |
| XCB-7 | − | + | ? | − | ND |
| XCH-2 | − | + | 5/q12–q13 | − | ND |
| XCH-3 | − | + | ? | − | ND |
| S101[c] | − | − | 22/q13 | − | low |
| S102 | − | − | 19/q13.4 | + | low |
| s110 | − | − | 12/p12–p13 | − | low |
| S111 | − | − | 2/p16–p21 | − | high |
| neo2Sc2[d] | − | − | D-group/q2 | − | ND |
| neo2Sc3[d] | − | − | D-group/q2 | − | ND |

[a]The chromosomal location indicated here were the ones which had the integrated mutant neo'-AAV's.
[b]The (+) means in the cell lines, the neo'-AAV DNA comigrated with the chromosome 19 specific cellular sequence which was cloned from the common AAV-cellular junction.
[c]These cell lines had both the wild type AAV and the neo'-AAV integrated during the neo'-AAV latent infection.
[d]The parental cell line of these neo'-AAV clones was D5 which already had the wild type AAV integrated before the neo'-AAV superinfection.

5.2. Modified AAV Vectors

The transfection of recombinant vectors containing an intact AAV genome, into cells infected with helper virus, results in rescue of the AAV genome from out of the plasmid vector followed by replication of the viral genome and encapsidation of viral DNA into mature virions. If the AAV coding region is deleted from the recombinant viral vectors and replaced by heterologous DNA sequences, the recombinant AAV vector can still complete the viral lytic cycle provided the AAV target sequences are intact and the REP and CAP proteins are provided in trans.

In the absence of helper virus, the AAV recombinant DNA will integrate into the host chromosome and remain there until the cell subsequently becomes infected with helper virus. In contrast to recombinant vectors that contain wild type AAV sequences and integrate into chromosome 19, recombinant AAV vectors lacking viral coding sequences integrate into additional regions of the genome.

A variety of host recombinant vector systems containing AAV viral sequences may be utilized equally well by those skilled in the art. The recombinant AAV vectors of the invention may contain varying amounts of AAV viral sequences. For example, the vectors may contain AAV viral sequences lacking the REP and/or CAP genes. In addition, the recombinant vectors will contain bacterial plasmid sequences necessary for conferring resistance to antibiotics such as ampicillin and tetracycline and sequences required for replication in *E. coli*. The vectors will also contain DNA sequences coding for a heterologous gene of interest, inserted between the appropriate transcriptional/ translational control sequences and polyadenylation signals. A variety of promoter/enhancer elements may be used depending on the level and tissue specific expression desired. Promoters derived from the genome of mammalian cells or produced by recombinant DNA or synthetic techniques may be used to provide for transcription of the inserted gene of interest.

Specific initiation signals are also required for efficient translation of inserted protein coding sequences. These exogenous translational control sequences which may include the ATG initiation codon and adjacent sequences can be of a variety of origins, both natural and synthetic. In addition, polyadenylation signals may be included to increase the stability of transcribed mRNAs.

Standard recombinant DNA methods may be used for a generation of eukaryotic expression vectors. These include in vitro recombinant DNA techniques, synthetic techniques and in vivo recombination/genetic recombination. See, e.g., the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y. For example, AAV viral sequences may be amplified in a PCR reaction using oligonucleotide primers that add an appropriate restriction endonuclease recognition site onto each end of the amplified viral DNA fragments. Alternatively, any restriction site desired may be produced by ligating nucleotide sequences encoding restriction endonuclease sequences onto the termini of the amplified targeting sequences. The targeting sequences may then be inserted into an expression vector having complementary cohesive termini.

Recombinant vectors containing inserted AAV sequences may serve as templates for mutagenesis studies using techniques well known to those skilled in the art. Such techniques include, but are not limited to, site-directed mutagenesis, construction of deletion mutants, or the use of PCR (polymerase chain reaction) to alter the AAV sequences. Altered nucleotide sequences which may be used in accordance with the invention include derivatives and analogs of the AAV sequences that are functionally equivalent in that they retain their ability to provide information, in cis, for replication, encapsidation, integration and rescue of recombinant DNA from the host cell genome. The AAV vectors of the invention need not necessarily integrate into chromosome 19 as is characteristic of wild type AAV vectors, but rather, may integrate into other specific regions of the human genome.

5.3. Generation of Recombinant Virus Stocks

To generate recombinant viral stocks, the recombinant vector is transfected into a host cell line that is capable of providing helper virus function, and supplying in trans AAV REP and CAP proteins. The REP and CAP proteins are required for replication and encapsidation of the linear recombinant DNA into mature viral particles and may be supplied in trans by transfection of a host cell line with a recombinant plasmid containing the genetic information necessary for coding of each of the proteins. DNA transfections may be carried out using any of a number of methods well known to those skilled in the art and may result in either transient or stable expression of the REP and CAP proteins. Techniques for transfection of DNA into host cells include DNA transfection by lipofection, electroporation or calcium phosphate precipitation [Ausubel, et al., 1989, in Current Protocols for Molecular Biology,]. For stable expression of the AAV REP and CAP proteins.

In addition to expressing the viral REP and CAP proteins, the host cell lines must be able to provide helper virus function. Both adenovirus and herpes simplex virus may serve as helper viruses for replication of DNA fragments containing the AAV targeting sequences. Any host cell permissive for infection by either of these two viruses or any virus that acts as a helper virus for AAV, may be used in the practice of the invention. Helper viruses which may be used, include but are not limited to Herpes simplex (HSV) varicella zoster, cytomegalovirus and Epstein-Barr virus. The multiplicity of infection (MOI) and the duration of the infection time will depend on the type of virus used and the cell line employed.

In a specific embodiment, described herein, 293 cells which had been transfected with a recombinant AAV expression vector, were infected with Ad5 at a MOI of 10. Forty-eight hours later the cells were frozen and thawed three times, and incubated for one hour at 56° C. to inactivate the adenovirus. The resulting cell lysate contains recombinant viral particles that may subsequently be used to infect cells or tissue of choice.

5.4. Characterization of Host Target DNA Sequences

A variety of techniques, routinely used by those skilled in the art, may be used for isolation and characterization of host target DNA sequences. For example, a λgt10 bacteriophage library may be constructed from genomic DNA prepared from independent latently infected cell lines. To identify the phage particles containing inserts of genomic DNA physically associated with AAV sequences, the library may be screened with a probe consisting of labeled AAV ITR sequences. Once positive clones have been isolated, the recombinant phage can be grown up and the DNA sequence of the insert can be determined using techniques commonly employed by those skilled in the art.

Alternatively, other methods may be used to identify and retrieve genomic target sequences. One such strategy for retrieving cellular junctions involves a protein filter binding procedure which makes use of the specific interaction between lambda repressor protein and its operator sequences, OR1 and OR2. The AAV recombinant vectors are engineered to contain the 47 basepair sequence containing the λ bacteriophage operator sites OR1 and OR2 (AAV-OR1-OR2). These sequences, when inserted into AAV vectors do not affect viral DNA replication or virus production.

AAV-OR1-OR2 infected latent cell lines may be established by infection of cells with recombinant virus. Genomic DNA, isolated from established latent cell lines may be digested with enzymes that do not recognize viral sequences. The digested DNA is incubated with purified λ repressor protein and any genomic fragments containing the OR1 and OR2 sequences will bind to the λ repressor protein. The genomic DNA may then be processed through a nitrocellulose membrane in a filter binding assay. The unbound DNA will be washed through the filter while the DNA/protein complex will be retained. DNA fragments retained on the nitrocellulose membrane, may then be cloned and sequenced to determine the cellular DNA junction sequences.

Alternatively, genomic DNA may be prepared from neo resistant cell lines. The genomic DNA is then cut with restriction endonucleases which do not cut within the AAV recombinant vector sequences. The DNA is then re-ligated and transformed into bacteria selecting for ampicillin resistance. Since the original AAV recombinant vectors contain the bacterial amp resistance gene and bacterial ori sequences, any resulting bacterial colonies will contain vector sequences and flanking host sequences. The vectors may be sequenced to determine the nucleotide sequence of the host sequences.

In a specific embodiment, described herein, Detroit 6 cells were infected with a recombinant viral stock generated from the recombinant vector designated pDD-Neo. Neo resistent clones were isolated and clonal cell line DD-16, was chosen for further analysis. Total genomic DNA from the DD-16 cell line was digested with the Bgl II restriction enzyme which fails to cut in the pDD-Neo vector. The digested genomic DNA was diluted, relegated and transformed in *E. coli*. Clone pDD16 (FIG. 10) was isolated and further characterized to determine into what region of the host genome the AAV sequences had integrated. Southern blot analysis indicated that the genomic sequences hybridized strongly to DNA from chromosome 2 and to lesser extent to DNA from chromosome 1 (FIG. 12). The host genomic DNA contained in the pDD16 vector were sequenced and those sequences are presented in FIG. 13.

5.5. Production of Transgenic Animals

The present invention provides for transgenic animals that carry the human chromosomal target sequences integrated into their genome. The invention provides for animals with target sequences in all their cells, as well as animals which carry the target sequences in some, but not all their cells, i.e., mosaic animals. The target sequences may be integrated as a single unit or in concatamers, e.g., head-to-head tandems or head-to-tail tandems. Animals of any species, including but not limited to mice, rats, rabbits, guinea pigs, pigs, micro-pigs, and non-human primates, e.g., baboons, squirrel monkeys and chimpanzees may be used to generate the transgenic animals of the invention. Any technique known in the art may be used to introduce the specific human target sequences into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., U.S.A. 82:6148–6152); gene targeting in embryonic stem cells (Thompson et al., 1989, Cell 56313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The transgenic animals generated using the methods described herein will be screened and evaluated to select those animals which contain human target sequences integrated into their genome. Initial screening to verify that integration of the transgene has taken place may be accomplished by Southern blot analysis or use of PCR techniques.

Founder animals that are produced, they may be bred, inbred, outbred, or crossbred to produce colonies of a particular animal. Examples of such breeding strategies include but are not limited to: outbreeding of founder animals with more than one integration site in order to establish separate lines; inbreeding of separate lines in order to produce compound transgenics; and crossing of heterozygous transgenic mice to produce mice homozygous for a given integration site. In addition, the transgenic animals that the invention provides for may be bred to different transgenic animals that have been bioengineered to serve as models for human genetic diseases. The resulting offspring may serve as animal model systems for proving the efficacy of AAV based vectors for use in treatment of specific human genetic diseases.

5.6. Uses of AAV Viral Vectors

The recombinant AAV vectors of the present invention, which contain a gene of interest, may be useful for therapeutic treatment of genetic diseases. The gene of interest may be the wild type complement of any mutated or defective gene and may be inserted into the recombinant AAV vectors so that its expression is controlled by its own endogenous natural promoter (e.g., so that expression is regulated normally) or by a heterologous promoter. More specifically, the invention relates to the use of vectors composed of specific AAV sequences that direct the integration of vector DNA and the gene of interest flanked by the AAV sequences, into specific regions of the human genome. The selection of vectors, i.e. selection of vectors with specific promoter/enhancer elements for regulated transcription, will depend on the targeted cell type and the required level of regulation of transcription.

The invention is also directed to the isolation and characterization of the human genomic DNA sequences that act as host target sequences for integration by vectors containing targeting sequences. Once identified, the target sequences may be used to develop transgenic animals containing the human chromosomal target sequences integrated into their genome. These transgenic animals will provide animal model systems for development and testing of AAV based genetic therapies. In addition, transgenic animals that have been developed as animal models for particular human genetic diseases, for instance, by expression of transferred genes or by insertional mutagenesis, may be bred to the transgenic animals containing the human target sequences. The resulting progeny may be used to test the use of AAV vectors for treatment of specific genetic diseases.

6. EXAMPLE: CONSTRUCTION OF NOVEL AAV RECOMBINANT VECTORS AND CHARACTERIZATION OF HOST TARGET SEQUENCES

The subsection below describes the construction and characterization of novel AAV recombinant vectors that contain AAV targeting sequences which direct the integration of recombinant vector DNA into unique specific sites in the human genome. The specific sites of integration were analyzed by methods such as in situ hybridization and Southern Blot analysis.

6.1. Materials and Methods 6.1.1. Tissue Culture

Human HeLa, 293, Detroit 6 (D6) cells were grown in monolayer cultures in Dulbecco's modified eagles medium (Gibco or Hazelton) with 10% fetal calf serum (Hyclone). D5 cells were a D6 clonal cell line latently infected with wild type AAV 2 and maintained in the same manner as D6 cells. HeLa spinner cells were grown as suspension culture in MEM with 5% calf serum (Gibco).

6.1.2. Preparation Viruses

Adenovirus type 5 strain d1301 was grown by infecting either 293 or HeLa cells with a multiplicity of infection (MOI) of 10. At 48 hours post-infection after the cytopathic effect was fully developed, the cells were collected with the medium. The virus preparation was frozen and thawed three times, aliquoted, and stored at −20° C. for use.

To measure the infectivity or titer of a given adenovirus stock, serial ten-fold dilutions of the virus lysate were prepared in serum free DMEM medium and 100 μl aliquots from each dilution were added to the 6-cm dishes containing confluent 293 cells. The adsorption proceeded for 1 hour and the cells were then overlaid with 5 ml of plaque assay solution containing 2% FCS in DMEM without phenol red, 0.64% Noble Agar (Difco) and 25 mM $MgC_2$ cooled to 42° to 45° C. After the agar solution was solidified at room temperature, the cells were incubated at 37° C. with 5% $CO_2$ for 5 days and another layer of plaque assay solution was overlaid on the dish to feed the cells. The plaques started to appear around one week after the initial infection and reached a plateau at two weeks. The final titer was determined either by directly counting the plaques or by staining the dish with neutral red to increase the contrast before counting.

For CsCl gradient purified adenovirus stock, a simpler method was utilized to estimate the virus titer. Briefly, a small aliquot (5 μl) of virus solution was diluted 60 fold with 295 μl of 0.5% SDS solution and incubated at 60° C. for 10 minutes. The optical destiny was taken at 260 nm. One $OD_{260}$ unit of the original virus stock solution equals approximately $50 \times 10^{12}$ virus particles per ml. Usually, 20 viral particles equals 1 infectious unit or plaque forming unit (p.f.u.).

AAV type 2 was obtained from ATCC (American Type Cell Collection) and maintained by infecting either 293 or HeLa cells with Ad5 at a MOI of 10 as the helper virus. At 48 hours post infection, the cells were collected with the medium, frozen and thawed three times. The virus lysate was heated to 55° C. for 1 hour to inactivate the adenovirus, aliquoted and stored at −20° C.

Since AAV can not form plaques during infection, the titer of the AAV virus stock was determined indirectly either by immunostaining of cells infected with the given AAV stock plus adenovirus with anti-capsid antibodies, or by extracting the AAV DNA from an aliquot of the given AAV virus stock, quantitating the DNA by Southern blot analysis with a known quantity of plasmid DNA and converting the DNA quantity into virus particle numbers. Usually, 5–100 viral particles equals 1 infectious unit (See, Samulski et al., 1987, J. Virology).

Mutant AAV stocks were made by co-transfection of mutant AAV plasmid constructs with the helper plasmid Pad/Ad (Samulski, 1989) into Ad5 infected 293 cells. A+ 48 hours post transfection, the mutant AAV viral preparation was handled exactly like wild type AAV. The titers of the mutant virus stocks were determined by counting the drug-resistant colonies for $neo^r$-AAV.

Infection with AAV virus and/or adenovirus was carried out as follows: For a 10-cm dish of cells, 0.5 ml DMEM containing adequate amount of AAV (10 m.o.i.) and/or adenovirus (10 p.f.u., plaque forming unit) was applied to the cells and incubated at room temperature for 1 to 2 hours with occasional rocking. The 0.5 ml DMEM was replaced by new DMEM containing 2% FCS. The cells were incubated at 37° C. with 5% $CO_2$ for 48 hours or desired times.

Transfection of recombinant AAV vector DNA was accomplished by either liposome or DEAE Dextran method. For the liposome method, 5 μg DNA was incubated with 2 ml of Opti-MEM (Gibco) at room temperature for 5 to 10 minutes. The DNA-liposome mixture was added to a 10-cm dish containing 2–3×10⁶ cells and 3 ml Opti-MEM. The cells were incubated at 37° C. for 4 hours or overnight. 5 ml DMEM containing 4% FCS was added and the incubation was continued for 48 hours before harvesting the cells.

For the DEAE Dextran method, 5 μg DNA was incubated with 2 ml of PBS containing 5% DEAE Dextran at room temperature for 5 minutes. The DNA mixture was added to the cells and incubated for 10 minutes at room temperature. The DNA mixture was then discarded and the cells were washed twice with 3 ml PBS followed by addition of 20 ml of DMEM containing 2% FCS. The incubation was carried out for 48 hours before harvesting the cells.

6.1.3. Construction of Recombinant Plasmids

Plasmid pXCBN-1 contains a Capsid gene with its functional promoter p40 and a selection marker TK-$neo^r$ gene in the plasmid psub201 (Samulski et al., 1987) backbone (FIG. 7). This plasmid was constructed by BstE II digestion in the middle of the genome and the sticky end was filled in with Klenow enzyme. The linear plasmid was further partial digested with XbaI on the left site of the AAV genome to delete the REP gene. At this site, a SbaI-HindIII (HindIII sticky end was filled in with Klenow enzyme) fragment from pDD-neo containing the TK-$neo^r$ gene was inserted to replace the REP gene. The putative transcription orientation of the TK-$neo^r$ gene was the same as the deleted REP gene. This plasmid was used to make the REP⁻CAP⁺ $neo^r$-AAV viral stock.

Plasmid pd152-91-Neo, which replaces the CAP gene with $neo^r$ gene while leaving the REP gene intact, is described in Hermonat and Muzyczka, 1984.

Plasmid pXCHN-1 contains a promoterless Capsid gene and a selection marker TK-$neo^r$ gene in the plasmid psub201 (Samulski et al., 1987) backbone (FIG. 8). This plasmid was constructed by HindIII digestion in the middle of the genome and the partial XbaI digestion on the left site of the AAV genome to delete the REP gene. At this site, XbaI-HindIII fragment from pDD-neo containing the TK-$neo^r$ gene was inserted to replace the REP gene. The putative transcription orientation of the TK-$neo^r$ gene was the same as the deleted REP gene. This plasmid was also used to make the REP⁻CAP⁺ $neo^r$-AAV viral stock.

Plasmid pNeo2 was made by deleting the entire REP and CAP genes and substituting them with a neomycin resistant ($neo^r$) gene. The resulting plasmid contains the two AAV 180 basepairs terminal repeats and the 140 base pairs adjacent to the right ITR.

Plasmid pDD-Neo was constructed as follows. Low molecular weight DNA from AAV and Ad5 infected cells was used as template for a PCR reaction with a single primer derived from D-sequence of AAV. The PCR was performed at 94° C. 1 min., 45° C. 30 seconds and 72° C. 1 min. for 35 cycles in a 50 ul reaction solution containing 20 mM Tris-HCl (pH 8.8), 1.5 mM MgCl, 50 mM KCl, 2.5% formamide, 100 uM dATP, dCTP and dTTP, 75 uM 7-deazo-dGTP, 25 uM dGTP, 1.5U AmpliTaq (Perkin Elmer Cetus), 1 ng AAV DNA and 100 pmole primer TR-1 (5'-GGAATTCAGGAACCCCTAGTGATGG3-3') (SEQ ID NO: 3). The PCR product was purified by agarose gel electrophoresis, cut with EcoRI and ligated with an EcoRI cut and dephosphorylated pGEM 3Z plasmid (Promega). The ligated plasmid was transformed into *E. coli* Sure strain (Stratagene). Positive clones named pDD's were screened for the presence of double-D terminal repeat and confirmed by dideoxy-sequencing with 7-deazo-dGTP substituted for dGTP (Sanger, F. et al., 1977, Proc. Natl. Acad. Sci. U.S.A. 74:5463–5467). Subsequently, a neo gene was cloned into the SalI site of pDD-2 resulting in the plasmid pDD-neo.

6.1.4. Isolation of Genomic and Viral DNA

A simple salting out method was utilized to extract the genomic DNA from tissue culture cells (Miller, et al., 1988). Briefly, cells collected from one 10 cm dish were resuspended in a 15 ml polypropylene centrifuge tube with 3 ml of nuclei lysis buffer (10 mM Tris-HCl, 400 mM NaCl and 2 mM EDTA, pH 8.2). The cell lysate was digested overnight at 37° C. by adding 0.2 ml of 10% SDS and 0.5 mg of proteinase K. Following digestion, 1 ml of saturated NaCl (6M) was added and the tube was vortexed vigorously for 15 seconds. The protein precipitate was pelleted by centrifugation at 3,500 rpm for 15 minutes and the supernatant containing the DNA was transferred to another tube. Two volumes of room temperature 100% ethanol was added to the tube and inverted several times. The fiber-like DNA precipitate was removed with the tip of a Pasture pipet, transferred to an 1.5 ml microfuge tube and washed with 75% ethanol followed by washing once with and 95% ethanol. The residual ethanol was removed as thoroughly as possible. The sample was vacuum dried for 1 minute (do not completely dry the DNA) and dissolved in 200 μl TE (pH 8.0) at 37° C. for several hours. The genomic DNA was clean and suitable for restriction digestion.

The Hirt method was intended to isolate the low molecular weight DNA such as viral or transfected plasmid DNA from tissue culture cells. The tissue culture medium was removed from a 6cm dish and 0.85 ml of Hirt solution (0.6% SDS, 10 mM Tris-HCl, pH 8.0, and 100 mM $Na_2$ EDTA pH 8.0) was added to the cells. The dish was then swirled about 10 times and the sticky cell lysate was poured into an 1.75 ml microfuge tube. 0.25 ml of 5M NaCl was added and mixed by inverting the tube several times. The sample was placed at 4° C. overnight and spun on a Sorvall High-Speed Centrifuge at 14,000 rpm for 30 minutes. The supernatant was transferred to a 2 ml microfuge tube and extracted with phenol, phenol-chloroform, and chloroform once each. The DNA was precipitated with an equal volume of isopropanol and spun at 4° C. on an Eppendorf centrifuge for 30 minutes. The DNA was washed once with 75% ethanol and dissolved in 50 µl of TE (pH 7.5) containing 10 g/ml RNase A.

For purification of viral DNA, adenovirus and/or AAV infected cells from one 10-cm dish were collected after full c.p.e. (cytopathic effect) was observed by centrifugation at 3,000×g for 10 minutes. The cell pellet was resuspended in 1.4 ml 50 mM Tris-HCl (pH 9.0) followed by addition of 100 µl of 100% ethanol and 10 µl of 20% sodium deoxycholate. The tube was inverted several times, incubated at room temperature for 1 hour and centrifuged at 4° C. at 10,000 rpm in an Eppendorf centrifuge for 15 minutes. The supernatant was recovered and 15 µl of RNase A (Sigma) (10 mg/ml stock), 3 µl of 1M $CaCl_2$ and $MgCl_2$ each, and 15 µl of DNase I (Sigma) (1 mg/ml stock) were added. The tube was inverted several times to mix thoroughly and incubated at 37° C. for 1 hour. After adding 80 µl of 10% Sarcosine (Sigma), the sample was heated at 70° C. for 10 minutes and cooled to 37° C. for 2 hours. Following addition of 1/20 volume of 3M NaAc and extraction with phenol, phenol-chloroform, and chloroform, the DNA was precipitated by 2.5 volumes of ethanol and washed twice by 75% ethanol. The dry DNA pellet was dissolved in 50 µl of TE (pH 8.0).

6.1.5. In Situ Hybridization

Glass slides were washed in methanol for about 30 minutes and then rinsed twice with distilled water. To test if the slides are clean, a thin layer of even water membrane should be observed on the surface after being taken out from the container. No hydrophobic spots should be observed. The cleaned slides were soaked in the ice-cold water before use.

The appropriate cells were seeded in 10-cm dishes and grown to ~80% confluence. Colcemid (Gibco) was added to a final concentration of 0.02 µg/ml and the cells were continued to incubate at 37° C. for 2–4 hours. After the incubation, many cells became round-up in shape due to the capture of these cells in mitotic phase. The culture medium was taken off and the cells were rinsed with 3 ml of PBS. After the rinse, 3 ml of PBS/EDTA was added to the cells. The dish was knocked against the edge of the tissue culture hood 10 to 20 times. At this point, numerous cells should be floating in the medium. If the cells are difficult to suspend, EDTA may be added to the PBS at a final concentration of 0.1 to 0.5 mM. The cells are then incubated until the desired cells are floating. A siliconized Pasture pipette was used to transfer the solution to a siliconized glass tube and the cells were centrifuged at 900 rpm on a table-top centrifuge for 8 minutes. The supernatant was discarded and about 0.5ml of the solution was left in the tube. The cells were resuspended in the remaining solution. A hypotonic solution (0.075M KCl in water) prewarmed to 37° C. was added to the cells dropwise up to about 1.5 ml. An additional 6 ml of the same solution was added to the tube and mixed by swirling. The tube was incubated in a water bath at 37° C. for 15 minutes. Timing was started at the beginning of adding hypotonic solution. The cells were centrifuged fixative and about 0.5 ml of the solution was left in the tube. After resuspension of the cells in the remaining solution, the fresh ice-cold fixative (3:1,Methanol:acetic acid) was added to the cells dropwise up to ~1.5 ml. An additional 6 ml of the same fixative was added to the tube and mixed by swirling. The tube was incubated on ice for 30 minutes and centrifuged at 900 RPM for 8 minutes. The supernatant was discarded and about 0.5 ml of the solution was left in the tube. These fixing steps were repeated for two more times. The fixed cells were resuspended in about 1 to 2 ml ice-cold fixative and placed on ice for chromosome spreading.

The fixed cells were dropped onto an ice-cold wet slide. Usually 2 to 4 drops is sufficient. If necessary, the slide was flamed immediately to facilitate the spreading. The chromosome spreads were air-dried and left overnight at room temperature. Finally, the slides were stored at −80° C. with desiccant until further use.

For high efficiency labeling of DNA probe, a two step nick translation method was utilized to prepare the non-radioactive labeled DNA probes either with biotin or digoxingenin conjugated dATP or dUTP. In this protocol, the nicking step and chain displacement labeling step were carried out separately. First, the nicking reaction was done by incubating DNA aliquots of 30 µg in 90 µl of nick translation buffer (50 mM Tris-HCl, pH 7.5, 50 mM NaCl, 10 MM $MgCl_2$, 1 mM DTT) with 54 ng of DNase I in 3-fold serial dilutions. The incubation was done at 37° C. for 15 minutes and stopped on ice. Then the reaction mixtures were heated at 65° C. for 1 hour. The sizes of DNase I treated samples were examined by alkaline agarose electrophoresis. The sample with a DNA fragment distribution from 500 to 800 nucleotides had the optimal size and was used in the next labeling reaction.

For biotin-labeling reaction, 3 µg DNase I treated DNA, 10 µl 0.4 mM biotin-14-dATP (BRL), 1.5 µl of 1 mM dCTP, dGTP and dTTP, 3 units of DNA polymerase I (DNase I activity free, BRL), 15 µl 10×nick translation buffer (500 mM Tris-HCl, pH 7.5, 500 mM NaCl, 100 mM $MgCl_2$ 10 mM DTT) were added in a final reaction volume of 150 ul. The reaction was performed at 16° C. overnight.

For digoxingenin-labeling reaction, 3 µg DNase I treated DNA, 15 µl of 0.35 mM Dig-dUTP (Borihinger Mannhein), 1.5 µl of 0.65 mM DTTP, 1 mM dCTP, and 1 mM DGTP, 3 units of DNA polymerase I (DNase I activity free, BRL), 15 µl 10×nick translation buffer (500 mM Tris-HCl, pH 7.5, 500 mM NaCl, 100 mM $MgCl_2$ 10 mM DTT) was added in a final reaction volume of 150 ul. The reaction was performed at 16° C. overnight.

The labeling reactions were stopped by adding 5 µl of 0.5M EDTA and 17 µl of 0.3M NaAc. The DNA was precipitated with 2.5 volumes of ethanol and washed twice with 75% ethanol. The labeled probe was dissolved in 60 µl of TE (pH 8.0) containing 0.1% of SDS and was then ready for use.

The fluorescent in situ hybridization was adopted from the methods of Lawrence et al (Lawrence et al., 1988) with modifications. Initially, the slides were incubated at 65° C. for 2 hours to harden the chromosomes. The slides were then acetylated in freshly made 0.1M triethanolamine (Sigma) and 0.25% acetic anhydride (Sigma) solution at room temperature for 10 minutes. Following rinse of the slides in 2×SSC twice, the chromosomes were denatured in 70% formamide-2×SSC (adjust to pH 7.0 with HCl) at 70° C. for 2 minutes. The denatured slides were immediately dehydrated through ice-cold 70%, 95% and 100% ethanol baths for 5 minutes each and then blown-dried with a hair dryer.

For each slide, 30 µl hybridization solution was used which contained 150 ng biotin-labeled or digoxingenin-labeled AAV or neo'DNA probe, 50 ng of biotin-labeled chromosome 19 probe (for double labeling of the chromosome), 15 µg sonicated salmon sperm DNA, 60 µg tRNA (Sigma). The above components in a microfuge tube were lyophilized and resuspended in 15 µl de-ionized formamide and then heated at 70° C. for 10 minutes. After denaturation, an equal volume (15 ul) of a solution containing 20% Dextran sulfate, 1% BSA and 4×SSC was added to the tube and mixed by vortexing. The hybridization solution was applied onto the slides, covered with coverslip and sealed with rubber cement. Hybridization was performed overnight in a humid chamber at 37° C. If the humid chamber was made of 50% formamide and 2×SSC, the slides were not required to be sealed. Following hybridization, the slides were soaked for 5 minutes in a wash solution containing 50% formamide and 2×SSC to loosen and peal the coverslips. Then the slides were washed twice for 30 minutes each at 37° C. in the above wash solution and finally in 1×SSC at room temperature for 30 minutes.

The slides were rinsed with 300 $\mu$l of RNaseH buffer (100 mM KCl, 20 mM Tris-HCl, pH 7.5, 1.5 mM $MgCl_2$, 0.7 mM EDTA, 50 $\mu$g/ml BSA, 1 mM DTT and 13 mM HEPES pH 7.5). 200 $\mu$l RNase H buffer containing RNaseH (BRL) 8 U/ml and RNaseA (Sigma) 10 $\mu$g/ml was applied to each slide, covered with parafilm and incubated in a humid chamber of warm water at 37° C. for 1 hour. The slides were rinsed twice with 1×SSC at room temperature for 10 minutes.

The slides were blocked with 200 $\mu$l blocking solution containing 4×SSC, 3% BSA and 0.1% Tween 20 (or Triton X 100) at room temperature for 10 minutes. For detection of biotin-labeled probe, 200 $\mu$l of detection solution containing 5 $\mu$g/ml fluorescein (FITC) labeled avidin (DCS or DN grade from Vector laboratories), 4×SC, 1% BSA and 0.1% Tween 20 was applied to the slides. For detection of digoxingenin-labeled probe, 200 ul of detection solution containing 1:25,000-fold diluted anti-digoxin monoclonal antibody (Sigma) in 4×SSC, 1% BSA and 0.1% Tween 20 was applied to the slides. The samples were cover with parafilm and incubate at room temperature for avidin and at 37° C. for antibody for 30 minutes in dark. After washed 3 times with 0.1% Tween 20 in 4×SSC at 37° C. for 10 minutes each, the anti-digoxin antibody treated slides were further incubated with Cy3 conjugated anti-mouse antibody (Gift from Dr. Alan Waggoner, Carnegie Mellon University Fluorescent Center) for 30 minutes and washed as above. After the final wash, both Cy3 or FITC treated slides were counter-stained either with propidium iodide (PI) or DAPI at the concentration of 0.2 $\mu$g/ml in PBS (pH 8.0) for 5 minutes and briefly rinsed with PBS. Finally, the slides were mounted with 25 $\mu$l of antifade solution and sealed on edges with rubber cement. The slides could be photographed immediately or stored at −20° C. for more than a week before photographing. The antifade solution was prepared by dissolving 100 mg p-phenylenediamine dihydrochloride (Sigma) in 10 ml PBS, adjusting the pH with 0.1N NaOH to pH 8.5, and mixing with 90 ml glycerol (Fisher, Enzyme grade). Aliquots (1 ml) of the antifade solution were stored at −80° C. in dark and were stable for over one year.

The fluorescent labeled chromosomes were visualized on a Nikon Labophot-2 epifluorescent microscope or a Zeiss Axiophot epifluorescent microscope. For simultaneous observation of FITC labeled viral signals (green) and propidiun iodide counter stained chromosomes (red), a filter combination was used consisting of exciter 485 nm, dichroic 510 nm, and barrier 420 nm. For Cy3 labeled viral signal (red), the filter combination was exciter 546 nm, dichroic 580 nm, and barrier 590 nm. For DAPI counter stained chromosomes, the filter combination was exciter 365 nm, dichroic 390 nm, and barrier 420 nm. Photographs were taken with Kodacolor Gold ASA400 film at exposure time from 30 seconds to 1 minute.

6.1.6. Southern Blot With Random Primer Labeled Probe

Southern blots were performed by digesting ~10 $\mu$g genomic DNA with appropriate restriction enzyme at a concentration of 50 to 10 units enzyme per $\mu$g of DNA and less than 0.2 $\mu$g DNA per microliter of reaction solution. After digestion, the DNA was concentrated by ethanol precipitation and resuspended in 20 to 30 $\mu$l of TBE electrophoresis buffer containing 0.02% each of bromophenoblue and Xylene cyanol tracking dyes. The digested DNA was separated by 1% agarose electrophoresis in TBE buffer at the voltage of <2V/cm. After electrophoresis was finished, the gel was stained with ethidium bromide and the photograph of the gel was taken. Subsequently, the gel was treated in 0.2N HCl for 5 to 10 minutes, rinsed with distilled water and denatured in 0.4N NaOH and 0.6 NaCl for 30 minutes with constant shaking. At the same time, a piece of Gene-Screen Plus membrane (DuPont) was prewet with distilled water and soaked in 0.4N NaOH and 0.6N NaCl solution. Following transfer, the nylon membrane was neutralized with 0.2M Tris-HCl, 2×SSC for 10 minutes and air-dried.

The prehybridization was carried out in 10 ml solution containing 1M NaCl, 1% SDS, 10% Dextran Sulfate at 65° C. for at least 30 minutes. The $^{32}$-P labelled DNA probe was made with a random primer kit (Boehringer Mannheim) and the salmon sperm DNA of 100 $\mu$g/ml were boiled in 1 ml of water and quickly chilled on ice. The probe mix was added to the prehybridized membrane in a hybridization bottle and incubated at 65° C. overnight. The membrane was washed three times with 2×SSC containing 1% SDS at room temperature for 5 minutes each, twice with 0.2×SSC containing 0.2% SDS at 65° C. for 30 minutes each, and finally twice with 0.1×SSC containing 0.1% SDS at room temperature for 5 minutes each. The membrane was wrapped with Saran Wrap and exposed against the X-Ray film (Kodak) with or without intensifying screen (Dupont).

Hybridization with $\gamma$-$^{32}$P-ATP end-labeled ITR oligonucleotide probes A-1 (5'TTGGCCACTCCCTCTCTGCG3', derived from the A region of ITR) and/or TR-I (5'GGAATTCAGGAACCCCTAGTGATGG3') were performed as follows: the membrane was prehybridized in 10 ml solution containing 5×SSC, 10×Denhardt's solution, 10% Dextran Sulfate and 5% SDS at 60° C. for at least one hour. 25 ng of $^{32}$P-end-labeled oligoprobe and 200 $\mu$g heat denatured salmon sperm DNA in 0.5 ml $H_2O$ were added. Hybridization was carried out at 60° C. overnight. The membrane was rinsed twice for 10 minutes each and washed twice for 30 minutes each at 60° C. with 5% SDS in 3×SSC. The membrane was rinsed once in 0.2×SSC at room temperature for 10 minutes, wrapped with Saran Wrap and exposed against X-ray film.

6.1.7. Cloning and Characterization of Specific Host Target Sequences

Recombinant vector pDD-Neo was integrated into the human genome of Detroit 6 cells. Neo resistent clonal cell lines were selected for and cell line DD16 was chosen for further analysis. The clone pDD16B was derived by digesting purified total genomic DNA from the DD16 cell line with Bgl II. The genomic DNA was diluted, relegated and used to transform E. coli. Transformants were selected for in the presence of ampicillin. The original clone pDD16 (FIG. 9) was 14 kb in length and contained two Bgl II restriction sites which yielded two fragments 8.5 and 5.5 Kb in length. pDD16B was derived by deleting the 5.5 Kb Bgl II fragment. The pDD16B plasmid inserts were sequenced using the method of Sanger et al. 1977, Prog. Natl. Acad. Sci. U.S.A. 74:5463–5467).

A 326 basepair probe for the left-hand junction from the Ssp I site (nt 190) to the Sma I site (nt 515 of the left handed junction), and a 184 basepair probe from the right-hand junction from the Sma I site (nt77 of the right-hand junction) were generated by restriction digestion of pDD16B followed by gel purification of the DNA fragments. The DNA fragments were labelled and used in Southern blot analysis to characterize the pDD-neo integration site.

6.2. Results 6.2.1. In Situ Analysis AAV Integration

In situ hybridization has been a very powerful tool for gene mapping. The advantage over Southern Blot analysis is the direct visualization of the target gene or fragment on the chromosomes. Fluorescent in situ hybridization is superior over the classical isotopic in situ methods, in that the former has finer resolution and higher reliability and allows simultaneous use of multicolored probes (Trask, 1991).

Three latent cell lines infected with wild type AAV were examined by fluorescent in situ hybridization. One cell line named Detroit 5 or D5 (Berns et al., 1975) was established 17 years ago from parental Detroit 6 cell, a human lung carcinoma cell line. The other two cell lines, G11 and H3, were derived from AAV infected HeLa cells. In the experiments, biotin-dATP labeled AAV probe and dioxigenin-dUTP or biotin-dATP labeled Sst probe (a DNA fragment which locates on chromosome 19 and 4 at the middle of the q arms, (Epstein et al., 1987) were utilized separately or simultaneously to hybridize with the chromosome spreads. Subsequently, the fluorescein labeled avidin (green) and Cy3 labeled anti-dig antibody (red) were applied to detect the signal of AAV and/or chromosome 19 signals (FIG. 29). In all three cell lines tested, the AAV viral DNA produced a signal on the tip of q arm of one chromosome 19 as confirmed by the co-localization of the Sst probe on the same arm.

The results demonstrate and confirm previous results that AAV integrates preferentially into the tip of q arm of chromosome 19. To address the question of whether the viral REP and CAP genes play any role in site-specific integration, REP$^-$CAP$^-$ recombinant AAV construct was made by deleting the entire REP and CAP genes and substituting them with a neomycin resistant (neo$^r$) gene. The resulting virus contains one TR on the left side, a neo$^r$ gene in the middle and one TR plus 140 bp noncoding AAV sequence on the right side (McLaughlin et al., 1988). The virus stock was prepared with a helper plasmid pAAV/Ad, which does not contain ITRs but the REP and CAP genes. Detroit 6 cells were infected with the virus and selected for G418 resistant clones.

Five independent G418 resistant cell clones were subjected to in situ fluorescent hybridization with either biotin-labeled neo probe alone or neo probe plus chromosome 19 probe (Epstein et al., 1987). One out of the five cell lines tested had the neo-AAV integrated into chromosome 19, similar to wild type AAV (FIG. 2, panel A & B for cell line S102). The rest of the cell lines had the neo-AAV integrated on different chromosomes as identified either by chromosome-specific probe or by chromosome banding and morphology. The results are shown respectively in FIG. 2, panel C & D for clone S110 on chromosome 12; panel E & F for clone S101 on chromosome 22; panel G & H for done S111 on chromosome 2; and panel I & j for clones D5 neo Sc#3 and panel K for D5 neo Sc#2 on a D-group chromosome. Since clones from panel I, J and K are different sub-clones from one original cell line they should be considered the same. One panel K, neo and AAV probes were simultaneously used, the wild type AAV could be easily observed on chromosome 19, while the neo-AAV had much weak signal, suggesting the neo-AAV had a lower copy number. The above results suggest that the inverted terminal repeat contains cis-sequences which can mediate site specific integration, although with a lower frequency of 20% (⅕) as revealed by in situ hybridization.

Since the REP$^-$CAP$^-$ AAV had a lower integration frequency into chromosome 19 than wild type AAV Rep gene is involved in the site specific integration a REP$^+$CAP$^-$ neo-mutant AAV was made by replacing the CAP gene with neo$^r$ gene while leaving REP gene fully functional (Hermonat and Muzyczka, 1984). REP$^+$CAP$^-$neo-AAV cell clones were produced by G418 selection and subjected to in situ hybridization. Ten cell lines were assayed. Two of them had the neo virus integrated into chromosome 19 (FIG. 3, panel A & B for clone HN63 and C & D for done XNR-4. In the remaining eight clones, the REP$^+$CAP$^-$neo-AAV's were not integrated into chromosome 19 (FIG. 3, panel E through T). For instance, Clone XNR-2 (panel G & H) had the neo virus on a site near the centromere of a chromosome morphologically like chromosome 5. Clone XNR-3 (panel I & J) had the virus at the middle of the p arm of a chromosome like chromosome 2, similar to the case in clone S111 (REP$^-$CAP$^-$, FIG. 2, panel G & H). Clone HN21 (panel S & T) had the neo-virus on a double minute, in which case the common AAV integration target sequence has been disrupted by the virus as previously revealed through southern blot (Kotin et al., 1990). Based on the fact that common fragile sites on 19q13 has been reported (Yunis and Soreng, 1984; Yunis et al., 1987), this double minute could be derived from chromosome 19 under drug selection. Further investigation is required to confirm this speculation.

The above results demonstrated that the functional REP gene in a mutant neo-AAV virus could not increase the integration efficiency into chromosome 19. Similar to REP$^-$CAP$^-$neo-AAV, the chromosome 19 specific integration efficiency by REP$^+$CAP$^-$neo-AAV is about 20% (²⁄₁₀), possibly 30% (³⁄₁₀) if the HN21 case is counted as a positive result. In contrast, the wild type AAV had a specificity greater than 80% (By compiling the published results from Kotin et al., 1990 and Samulski, et al. 1991, we noticed that 15 out of 18 wild type AAV cell lines had the proviruses integrated into chromosome 19 sequence).

To address the issue of whether the capsid gene plays any role in the high-efficiency integration into chromosome 19 by AAV two mutant constructs were made by replacing the REP gene with neo gene while retaining the capsid gene intact. In one plasmid the capsid gene is driven by the native p40 promoter. In the other plasmid the p40 promoter is deleted resulting in a promoterless capsid gene. The REP$^-$CAP$^+$neo-AAV viruses was prepared by conventional method. Human Detroit 6 cells were infected by the recombinant viruses and the G418 resistant single clones were isolated. The clones made from the virus with the functional p40 promoter are named XCB-1 through XCB-12, while the ones made from the promoterless capsid virus are named XCH-1 to 10.

Five G418 resistant clones were examined by in situ chromosome hybridization. One of them is XCB-2, which previously screened positive by PCR with primers Jus-3 (a cellular junction primer from the AAV integration hot spots) and neo-3 (a primer which is at the left end of the neo virus and points outward). The other four clones are XCB-5, XCB-7, XCH-2 and XCH-3, that were PCR negative. Except for XCH-3 from which we could not detect the viral signal by in situ hybridization, the other four cell lines showed viral signal on one chromosome respectively.

XCB-2 had the virus integrated into chromosome 19 (FIG. 33, panel A & B). XCB-5 had the virus on the tip of the long arm of an unidentified chromosome (FIG. 33, panel C & D), while XCB-7 had the virus on the middle of the long arm of a different chromosome (FIG. 33, panel E & F). XCH-2 had the virus integrated into a site close to the centromere at the long arm of a chromosome (FIG. 33, panel G & H), possibly chromosome 5 by morphology. Noticeably, previous in situ hybridization with a REP+CAP−neo-AAV cell line (XNR-2 see FIG. 32, panel G & H) showed a very similar result: the neo-virus is at the same cytogenetic location of a similar, if not the same, chromosome as in XCH-2 (FIG. 4, panel G & H). Therefore, the REP−CAP+neo-AAV viruses had a similar specific integration efficiency into chromosome 19 of about 25% (¼) as revealed by fluorescent in situ hybridization.

6.2.2. Genomic Southern Analysis

Although fluorescent in situ hybridization can directly visualize the physical location on the chromosomes at the microscopic level, it does not have the sensitivity and resolution at the molecular level when compared with Southern Blot analysis.

In order to confirm the in situ fluorescent hybridization results, those neo-AAV latent cell lines already analyzed by in situ hybridization were further characterized by genomic southern blot. The genomic DNAs from various neo-AAV cells were digested with restriction enzyme BamHI for the reason of consistency and easier interpretation, since this enzyme was used in a previous study to characterize the integration of some 22 latent AAV cell lines (Kotin et al., 1990).

In that study, the genomic blot was probed with a cloned common AAV-cellular junction fragment located on chromosome 19, which displays as a single 2.6 kb BamHI band by southern blot in the parental cells but is disrupted in about 80% of the wild type AAV latent cell lines (Kotin et al., 1990, Samulski et al., 1991). The same methodology was used to analyze the mutant neo-AAV cell lines. After probing with the junction fragment, the same blot was stripped with sodium.

In nine REP+CAP− cell lines tested, three of them had the chromosome 19 junction fragments comigrate with the neo fragments (XNR-4, XNR-5 and HN-63, see lane 4, 5 and 9 in FIG. 5, suggesting the physical linkage of the viral and the cellular junction sequences. Among these three cell lines, XNR-4 and XHN-63 (lane 4 and 9) had the single upper shifted cellular junction band comigrate with the single neo band. Consistent with the southern results, the proviruses in these two cell lines were also visualized by in situ hybridization on the tip of q arm of one chromosome 19. In contrast, the provirus in clone XNR-5 was located on the tip of the long arm of a chromosome different from 19 by in situ hybridization (FIG. 3, panel K & L), while the southern blot showed comigration of the viral- and 19-sequences (lane 5, in FIG. 5). In addition, PCR with a neo primer and a common junction primer gave rise to positive results in this cell line as well as XNR-4 (data not shown), suggesting the physical linkage. Careful examination of the chromosome spreads from this cell line did not reveal any neo signal on chromosome 19. Based on the above observation and the southern result that the two upper shifted cellular junction bands comigrate with the two neo bands and no other neo band is found, two interpretations could be made. First, the neo-AAV virus indeed integrated into the chromosome 19 common integration site in cell line XNR-5. Second, some translocation event might have occurred, although we do not know it was before or after the viral integration.

For cell line HN21, the in situ hybridization demonstrated that the neo-AAV locates on a double minute. However, southern blot showed the disruption of the cellular junction fragment (Kotin et al., 1990). It is therefore possible that the double minute is derived from chromosome 19 under drug selection.

In cell line XNR-3, there exists a down shifted band which hybridize to the junction fragment (lane 3 in FIG. 5). This band, however, does not comigrate with the single neo band. Consistently, the in situ hybridization reveal the neo-AAV provirus on chromosome 2 other than 19 (FIG. 3, panel I & J). Therefore, the neo-AAV did not integrate into the chromosome 19 site in this cell line. In addition, dot blot of this cell line with the AAV capsid probe revealed the presence of wild type AAV, which was originated from the wild type AAV helper virus generated during the preparation of neo-AAV. The altered cellular band could be possibly caused by the wild type instead of the neo-AAV integration.

In summary, the southern blot results are in good agreement with the in situ hybridization results. Thus, the assays from eight out of ten cell lines are completely consistent: two 19-specific integrations (XNR-4 and HN-65) and six non-19 integrations (XNR-1, 2, 3, 6, 7, and 8). The remaining two cases revealed some new phenomena, thus, the cytogenetic rearrangement such as translocation and double minutes. Currently it is not known if these rearrangements took place before or after the AAV integration and if they were caused by the drug selection or simply by AAV integration.

Among the five REP-CAP− neo-AAV cell lines examined by in situ hybridization, the neo-AAV was shown to have integrated into chromosome 19 in only one cell line (S102). Southern analysis of S102 confirmed the result by demonstrating that the single upper shifted cellular junction band comigrated with the single neo band (lane 14 in FIG. 5). PCR reactions with the junction primer and two neo primers pointing either to the right ITR or the left ITR also gave positive results (data not shown). The other four cell lines had the neo-AAV integrated into the non-19 chromosomes reveal by in situ hybridization also failed to show positive results for comigration of chromosome 19 and neo sequences by southern blot (FIG. 5). For instance, in cell lines S110 (lane 15 in FIG. 5) and S111 (Kotin et al 1990), there is no disruption of the chromosome 19 sequence in the genomic blot. Consistently, the in situ results visualized the neo-AAV provirus respectively on chromosome 12 and 2. For cell line D5neo Sc#3, the parental cell D5 had two altered chromosome 19 cellular bands caused by the wild type AAV integration (Kotin et al., 1989). After superinfection with REP−CAP− neo-AAV, the southern blot pattern of the cellular fragment remained unchanged (lane 12, FIG. 5), suggesting no additional disruption by the neo-AAV. Careful superimposition and alignment of the films probed with the junction or the neo fragment ruled out the possible comigration of the single neo band with the largest cellular band. In situ hybridization also showed the neo-AAV on a D-group chromosome. In the case of cell line S101, the single neo band did not comigrate with the disrupted 19 sequences. The coexisting wild type AAV in this cell line (Mclaughlin et al., 1988) could possibly cause the alteration of the chromosome 19 site.

The REP−CAP+ AAV cell lines indicate similar results. The in situ hybridization results and the southern blot results are consistent with each other. In cell line XCB-2 (lane 16 in FIG. 34) two of the three neo bands comigrated with the two upper shifted cellular bands an& in situ hybridization revealed the location of the neo-AAV provirus on chromosome 19. In the remaining four cell lines with non-19 integration, no chromosome 19 sequence was disrupted and no proviruses visualized on chromosome 19.

In conclusion, the southern blot results and in situ hybridization results confirmed the results summarized in Table 1 (p. 13 of the specification).

Wild type AAV integrates into chromosome 19 with a high efficiency. All five cell lines assayed by in situ hybridization have the wild type AAV on chromosome 19. These results are also in agreement with the Southern Blot experiments (Kotin et al., 1990; Samulski et al., 1991), in which the AAV proviral sequences have been shown to comigrate with the cellular junction sequence, indicating site-specific integration.

With a lower efficiency of 20%, the double-mutant AAV (REP$^-$CAP$^-$) without any viral coding sequences can still integrate into chromosome 19, suggesting that inverted terminal repeats contain necessary and probably sufficient cis-sequence for site specific integration.

A functional REP gene in the mutant AAV (REP$^-$CAP$^-$) does not increase the specific integration efficiency significantly suggesting that the REP gene alone is not responsible for high-frequency specific integration.

Similarly, a functional CAP gene in the mutant AAV (REP$^-$CAP$^+$) does not increase the specific integration efficiency either, suggesting that neither REP nor CAP gene alone will contribute to the high efficiency integration into chromosome 19. Therefore, the integration event seems to require both REP and CAP position to function synergistically.

Figure 14C:
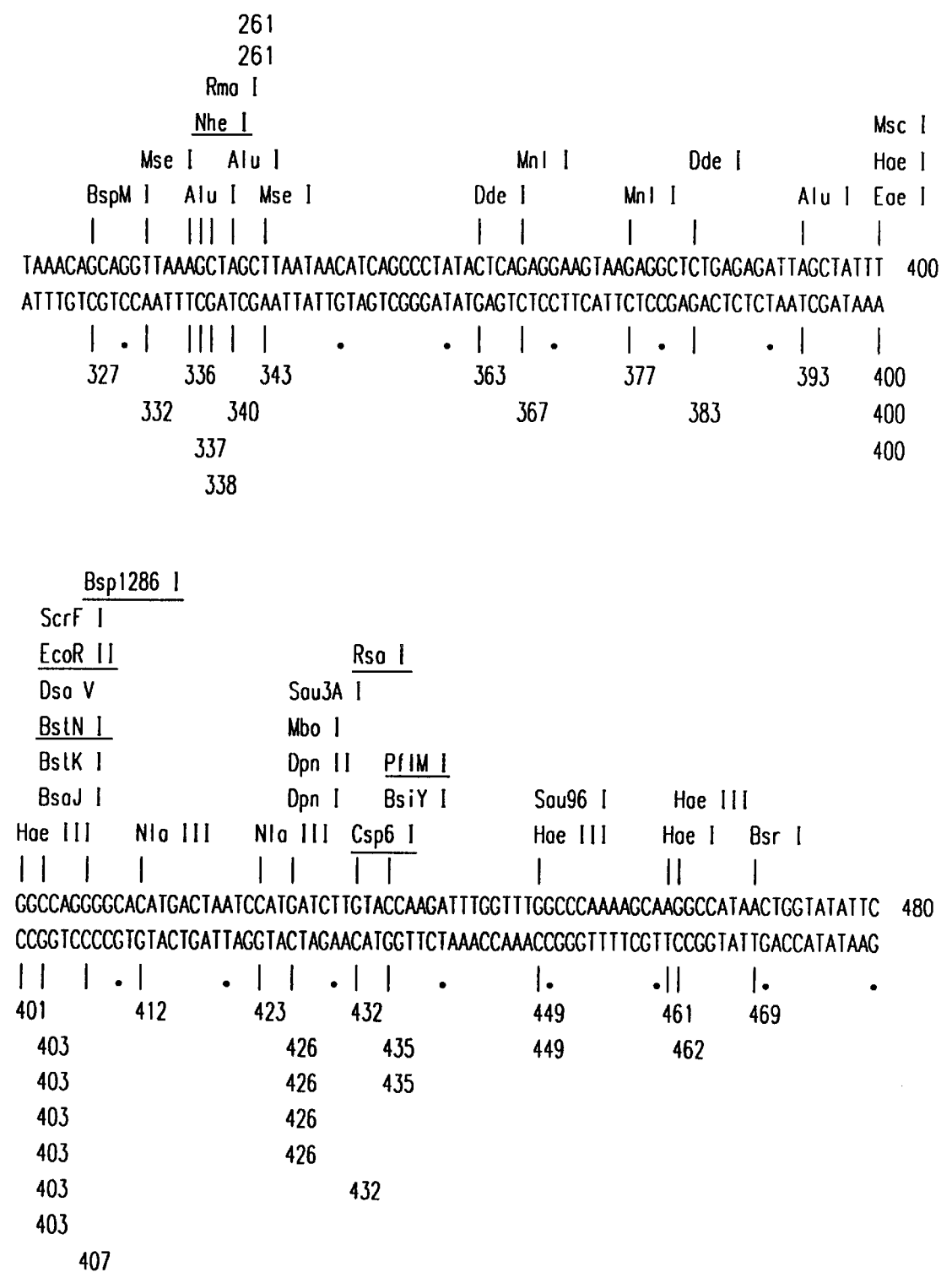

6.2.3. Cloning and Characterization of Specific Target Host Sequences pDD16B is a derivative of a clone of the recombinant AAV provirus pDD-Neo that has integrated into the human genome in Detroit 6 cells in low or single copies. Sequencing of pDD16B indicated that the AAV terminal repeats were not completely intact on either the left-hand or right-hand junctions. The left-hand junction contained 50 basepairs of the terminal repeat, while the right-hand junction contained 80 basepairs of the terminal repeat (FIGS. 13 and 14). In addition to the terminal repeat sequences, pDD16B contains 175 basepairs of genomic DNA on the right-hand junction with pDD-Neo, and approximately 4.3 kb of genomic DNA on the left-hand junction with pDD-Neo.

A 326 basepair probe for the left-hand junction from the Ssp I site (nt 515 of the left-hand junction Strider map), and a 184 basepair probe from the right-hand junction from the Sma I site (nt 77 of the right-hand junction Strider map) to the Bgl site (nt 260) were generated by restriction digestion of pDD16B and gel purification of the restriction fragments. These probes were used to characterize the location of the integration site for pDD-Neo.

FIG. 11 depicts a Southern blot of Bgl II-digested genomic DNA from latent Detroit 6 cell lines containing low or single copies of the pDD-Neo provirus. This blot was probed with the DNA fragment from the left-hand junction of pDD-Neo described previously. The probe hybridized to a 7 kb pre-integration DNA fragment in all cell lines. In addition, the probe also hybridized to a 8.5 kb DNA fragment in lanes 8 and 10. Lane 10 is genomic DNA from which pDD16B was originally derived. The size of this additional DNA fragment that the left-hand junction probe hybridizes to in lane 10 is the same as that of the pDD16B plasmid. The size of the additional DNA fragment that the left-hand junction probe hybridizes to in lane 8 appears to slightly larger than the DNA fragment seen in lane 10, and suggests that an independent provirus present in the latent cell line (lane 8) has also targeted the same chromosomal sequence as the provirus derived from lane 10, indicating that this is a preferred integration site.

FIG. 12 depicts a Southern blot of somatic cell hybrid panels containing DNA from individual human chromosomes digested from Bam HI. This blot was also probed with the DNA fragment derived from the left-hand junction. The probe hybridized to a single Bam HI DNA fragment in total human male and female DNA (lanes 1 and 2), and did not hybridize to DNA from mouse or hamster, indicating this sequence is unique. The probe strongly hybridized to DNA from chromosome 2, and to a lesser extent to DNA from chromosome 1. The left-hand junction probe showed no significant hybridization to any other human chromosome. These data strongly suggest that the sequence is not represented throughout the human genome and that the vector is targeting to unique or low copy cellular sequences present in this example primarily on chromosome 2 and 1.

Deposit of Microorganisms

The following cell lines have been deposited with the American Type Culture Collection, (ATCC), Rockville, Md. and have been assigned the following accession members:

| Cell Line | Date of Deposit | Accession No. |
| --- | --- | --- |
| XNR-2 | May 26, 1995 | CRL-11903 |
| XNR-3 | May 26, 1995 | CRL-11902 |
| Neo$_2$SC$_3$ | May 26, 1995 | CRL-11901 |

The present invention is not to be limited in scope by the specific embodiment described herein, which are intended as single illustrations of individual aspects of the invention, and functionally equivalent methods and components are within the scope of the invention. Indeed, various modifications of the invention, in addition to those shown and described herein will become apparent to those skilled in the art form which the foregoing description and accompanying drawings. Such modifications are intended to fall within the scope of the appended claims.

What is claimed is:

1. A recombinant AAV vector lacking AAV REP or CAP viral coding regions that upon transfection into a human cell integrates into the p16–p21 region of human chromosome 2, the q12–q13 region chromosome 5, the p12–p13 region of human chromosome 12. the q13 region of human chromosome 22, or the q2–q3 region of a human D-group chromosome, comprising (i) AAV nucleic acid sequences that include at least an adeno-associated virus left and right ITR sequence; and (ii) a nucleic acid sequence encoding a protein of interest.

2. A method of replicating and encapsidating a recombinant DNA molecule into an AAV virion, comprising:
   (a) culturing a eukaryotic cell containing (i) a helper virus, (ii) a recombinant nucleic acid that directs the expression of AAV REP and CAP proteins in the eukaryotic cell, and (iii) the recombinant AAV vector of claim 1 whereby the recombinant AAV vector is replicated and assembled into AAV virions; and
   (b) collecting virions produced.

3. The method according to claim 2 in which the helper virus is an adenovirus.

4. The method according to claim 2 in which the helper virus is a herpes simplex virus.

5. The method according to claim 2 in which the recombinant nucleic acid encoding the AAV REP and CAP proteins is a plasmid vector comprising:

(a) promotors which control the expression of the AAV REP and CAP RNA;

(b) translation initiation signals for the REP and CAP mRNA;

(c) DNA sequences encoding the REP and CAP proteins; and (d) transcriptional termination signals.

6. A cultured host cell which produces stocks of recombinant adeno-associated viruses and produced by a method comprising:

(a) culturing said host cell containing (i) a helper virus, (ii) a recombinant nucleic acid that directs the expression of AAV CAP and REP proteins in the host cell, and (iii) the recombinant DNA vector of claim 1 whereby the recombinant DNA vector is replicated and assembled into AAV virions; and (b) collecting virions produced.

7. An isolated polynucleotide comprising a human genomic nucleotide fragment which maps to the q12–q13 region of chromosome 5, wherein said fragment contains integrated AAV nucleic acid sequences.

8. An isolated polynucleotide comprising a human genomic nucleotide fragment which maps to the p16–p12 region of chromosome 2, wherein said fragment contains integrated AAV nucleic acid sequences.

9. An isolated polynucleotide comprising a human genomic nucleotide fragment which maps to the q2–q3 region of a D-group chromosome, wherein said fragment contains integrated AAV nucleic acid sequences.

10. An isolated polynucleotide comprising a human genomic nucleotide fragment which maps to the p12–p13 region of chromosome 12, wherein said fragment contains integrated AAV nucleic acid sequences.

11. An isolated polynucleotide comprising a human genomic nucleotide fragment which maps to the q2–q3 region of a D-group chromosome, wherein said fragment contains integrated AAV nucleic acid sequences.

12. An isolated polynucleotide comprising a human genomic nucleotide fragment which maps to the q13 region of chromosome 22, wherein said fragment contains integrated AAV nucleic acid sequences.

13. A isolated human cell comprising genomic nucleotide sequences into which adeno-associated virus nucleic acid sequences are integrated wherein the genomic nucleotide sequences map to the q12–q13 region of chromosome 5.

14. A isolated human cell of comprising genomic nucleotide sequences into which adeno-associated virus nucleic acid sequences are integrated wherein the genomic nucleotide sequences map to the p16–p21 region of chromosome 2.

15. A isolated human cell comprising genomic nucleotide sequences into which adeno-associated virus nucleic acid sequences are integrated wherein the genomic nucleotide sequences map to the q2–q3 region of a D-group chromosome.

16. A isolated human cell comprising genomic nucleotide sequences into which adeno-associated virus nucleic acid sequences are integrated wherein the genomic nucleotide sequences map to the p12–p13 region of chromosome 12.

17. A isolated human cell comprising genomic nucleotide sequences into which adeno-associated virus nucleic acid sequences are integrated wherein the genomic nucleotide sequences map to the q2 region of a D-group chromosome.

18. A isolated human cell comprising genomic nucleotide sequences into which adeno-associated virus nucleic acid sequences are integrated wherein the genomic nucleotide sequences map to the q13 region of chromosome 22.

19. A method of integrating a nucleic acid sequence into the p16–p21 region of human chromosome 2, the p12–p13 region of human chromosome 12, the g13 region of chromosome 22, the q12–q13 region of human chromosome 5 or the 92 region of the human D-group chromosome, comprising transfecting a human cultured human cell with the recombinant AAV vector of claim 1, wherein said nucleic acid sequence is integrated.

20. A method of integrating a nucleic acid sequence into the p16–p21 region of human chromosome 2, the p12–p13 region of human chromosome 12, the q13 region of chromosome 22, the g12–g13 region of human chromosome 5 or the q2 region of the human D-group chromosome, comprising infecting a cultured human cell with the recombinant adeno-associated virus obtained according to the method of claim 2 or 6, wherein said nucleic acid sequence is integrated.

* * * * *

UNITED STATES PATENT AND TRADEMARK OFFICE
CERTIFICATE OF CORRECTION

PATENT NO. : 5,773,289
APPLICATION NO. : 08/469552
DATED : June 30, 1998
INVENTOR(S) : Richard Jude Samulski et al.

It is certified that error appears in the above-identified patent and that said Letters Patent is hereby corrected as shown below:

Column 25, line 1: "(a) promotors which controls the expression of the AAV" should read --(a) promoters which control the expression of the AAV--

Column 25, line 24: "genomic nucleotide fragment which maps to the p16-p12" should read --genomic nucleotide fragment which maps to the p16-p21--

Column 26, line 28: "region of human chromosome 12, the g13 region of chro-" should read --region of human chromosome 12, the q13 region of chro---

Column 26, line 30: "the 92 region of the human D-group chromosome, compris-" should read --the q2 region of the human D-group chromosome, compris---

Column 26, line 31: "ing transfecting a human cultured human cell with the" should read --ing transfecting a cultured human cell with the--

Column 26, line 37: "mosome 22, the g12-g13 region of human chromosome 5 or" should read --mosome 22, the q12-q13 region of human chromosome 5 or--

Signed and Sealed this

Twenty Second Day of April, 2008

JON W. DUDAS
*Director of the United States Patent and Trademark Office*